(12) United States Patent
Liaw et al.

(10) Patent No.: US 8,399,207 B2
(45) Date of Patent: Mar. 19, 2013

(54) MONOCLONAL ANTIBODIES AGAINST OSTEOPONTIN

(75) Inventors: Lucy Liaw, South Portland, ME (US); Ah-Kau Ng, Portland, ME (US)

(73) Assignee: Maine Medical Center, Portland, ME (US)

( * ) Notice: Subject to any disclaimer, the term of this patent is extended or adjusted under 35 U.S.C. 154(b) by 0 days.

(21) Appl. No.: 12/983,650

(22) Filed: Jan. 3, 2011

(65) Prior Publication Data

US 2011/0165697 A1    Jul. 7, 2011

Related U.S. Application Data

(63) Continuation of application No. 11/978,796, filed on Oct. 30, 2007, now Pat. No. 7,867,725.

(60) Provisional application No. 60/855,181, filed on Oct. 30, 2006.

(51) Int. Cl.
| | |
|---|---|
| *G01N 33/543* | (2006.01) |
| *G01N 33/574* | (2006.01) |
| *G01N 33/577* | (2006.01) |
| *C07K 16/18* | (2006.01) |
| *C12N 5/20* | (2006.01) |

(52) U.S. Cl. ...... 435/7.23; 435/7.1; 435/7.92; 435/7.94; 435/70.21; 435/336; 435/344; 435/518; 435/548; 435/64; 530/388.24; 530/388.8; 530/388.85; 530/391.1

(58) Field of Classification Search .............. 435/7.1, 435/7.23, 7.92, 7.94, 70.21, 336, 344; 436/518, 436/547, 548, 64; 530/388.24, 388.8, 388.85, 530/389.1, 389.2, 389.7, 391.1
See application file for complete search history.

(56) References Cited

U.S. PATENT DOCUMENTS

| | | | |
|---|---|---|---|
| 6,414,219 | B1 | 7/2002 | Denhardt et al. |
| 7,867,725 | B2 * | 1/2011 | Liaw et al. ............ 435/7.23 |
| 2005/0009120 | A1 | 1/2005 | Mok et al. |

OTHER PUBLICATIONS

Kon et al. Antibodies to Different Peptides in Osteopontin Reveal Complexities in the Various Secreted Forms. Journal of Cellular Biochemistry. Apr. 2000, vol. 77, pp. 487-498, see entire document.
Agnihotri et al. Osteopontin, a Novel Substrate for Matrix Metalloproteinase-3 (Stromelysin-1) and Matrix Metalloproteinase-7 (Matrilysin). The Journal of Biological chemistry. Jul. 27, 2001, vol. 276, No. 30, pp. 28261-28267.
Hotta et al. Detection of Various Epitopes of Murine Osteopontin by Monoclonal Antibodies. Biochemical and Biophysical Research Communications. 1999, vol. 257, No. 1, pp. 6.
Kon et al. Mapping of Functional Epitopes of Osteopontin by Monoclonal Antibodies Raised Against Defined Internal Sequences. Journal of Cellular Biochemistry. 2002, vol. 84, pp. 420-432.
Vordermark, et al, "Plasma osteopontin levels in patients with head and neck cancer and cervix cancer are critically dependent on the choice of ELISA system" BMC Cancer, 6(1):207, 2006.
Engvall, Eva, et al., Enzyme-linked immunosorbent assay. II. Quantitative assay of protein antigen, immunoglobulin G, by means of enzyme-labelled antigen and antibody-coated tubes. Biochim Biophys Acta, 251(3):427-434, 1971.
Kohler, G. and Milstein, C., Nature, 256(5517):495-7 1975.
Mark, et al., J Histochem Cytochem, 35(7):707-716, 1987.
Mark, M.P., et al., Cell Tissue Res, 251:23-30, 1988.
Liaw, et al., Circ Res, 74(2):214-24 1994.
Liaw, et al., J Clin Invest, 101(7):1468-78 1998.
Rudland, et al., Cancer Res, 62(12):3417-3427, 2002.
Fedarko, et al., Clin Cancer Res 7(12):4060-4066, 2001.
Gao, Y.A., et al., Matix Biol, 23(7):457-466, 2004.
Senger, D.R., et al., Ann NY Acd Sci, 760:83-100, 1995.
Senger, D.R., et al., Am J Pathol, 149(1):293-305, 1996.
Senger D.R., et al., Biochem Biophys Acta, 1314(1-2):13-24, 1996.
Bayless, K.J., et al., J Biol Chem, 276(16):13483-13489, 2001.
Green, P.M., et al., FEBS Lett, 503(1):75-79, 2001.
Smith, L.L., et al., Exp Cell Res, 242:351-360, 1998.
Yokosaki, Y., et al., Matrix Biol, 24(6):418-427, 2005.

* cited by examiner

*Primary Examiner* — Gail R Gabel
*Assistant Examiner* — James L Grun
(74) *Attorney, Agent, or Firm* — Pierce Atwood LLP; Kevin M. Farrell; David J. Wilson

(57) ABSTRACT

The present invention relates to reagents and methods for the detection of osteopontin fragments and distinguishing them from each other and from the full-length osteopontin protein. The present invention also relates to assays for the determination of the presence of osteopontin fragments in samples obtained from subjects and, further, the correlation of osteopontin fragment levels fragment levels with disease detection, progression and prognosis.

6 Claims, 19 Drawing Sheets

100x

50x

200x

MONOCLONAL ANTIBODIES AGAINST OSTEOPONTIN

The Applicants acknowledge the National Cancer Institute of the National Institutes of Health for financial support of this work under Grant No. CA129849. The Federal Government has a nonexclusive, nontransferable, irrevocable license in this invention on behalf of the United States. [37 CFR 401.14(b)].

BACKGROUND

Osteopontin (OPN) is a secreted phosphoprotein that is associated with cancer, cardiovascular disease, renal injury and inflammation. One of the first descriptions of osteopontin was as a secreted phosphoprotein (spp 1) found at elevated levels circulating in the serum of cancer patients. Since that time, numerous studies have shown upregulated expression of osteopontin in various human cancers. Not limited to cancer, osteopontin expression is associated with various tissue injury and human diseases. Several clinical studies have been performed to assess the potential of osteopontin to serve as a clinical marker for disease progression or prognosis in human breast cancer. The results of these studies show that there is a significant overlap of osteopontin with other variables associated with patient outcome including high histological grade, c-ErbB3 and p53 (Rudland, et al., Cancer Res, 62(12): 3417-3427, 2002). Significantly, these breast cancer patients were studied for 14-20 years of follows up and, while the low-osteopontin group had a median survival of >228 months, the high-osteopontin group had a median survival of 68 months, suggesting predictive value of osteopontin levels in long-term patient outcome. Other studies suggest that, in addition to breast cancer, elevated osteopontin in the serum is associated with prostate and lung cancer (Fedarko, et al., Clin Cancer Res 7(12):4060-4066, 2001).

There are several characteristics of osteopontin that make it a valuable candidate as a biomarker for disease. The protein is secreted in body fluids and can be found in, e.g., plasma and serum, human milk and urine. There are available ELISA-based assays to test for osteopontin protein levels. However, multiple modified fragments of osteopontin exist that represent proteolytically cleaved fragments of the parent molecule. These cleaved fragments are distinct functionally (Gao, Y. A., et al., Matix Biol, 23(7):457-466, 2004; Senger, D. R., et al., Ann NY Acd Sci, 760:83-100, 1995; Senger, D. R., et al., Am J Pathol, 149(1):293-305, 1996; Senger D. R., et al., Biochem Biophys Acta, 1314(1-2):13-24, 1996; Bayless, K. J., et al., J Biol Chem, 276(16):13483-13489, 2001; Green, P. M., et al., FEBS Lett, 503(1):75-79, 2001; Smith, L. L., et al., Exp Cell Res, 242:351-360, 1998; Yokosaki, Y., et al., Matrix Biol, 24(6):418-427, 2005), they occur in vivo and are generated through the catalytic activity of proteases such as thrombin and the matrix metalloproteinases that are known to be associated with tumor progression. Indeed, the question of whether these osteopontin fragments wound provide a more accurate assessment of clinical tumor burden, progression or patient outcome is an important issue that has not been addressed. Part of the limitation is that there are not reagents that will specifically detect osteopontin fragments and distinguish them from each other and the full-length protein. Thus far only SDS-PAGE analysis followed by immunoblotting with anti-osteopontin antibodies can show fragment presence in clinical samples. However, even this method has significant drawbacks since antibodies for specific OPN fragments may not exist. For example, a recent report showed that results of commercially available ELISA assays for osteopontin in neck, head and cervix cancer patents are dependent upon the assay kit used (Vordermark, et al, "Plasma osteopontin levels in patients with head and neck cancer and cervix cancer are critically dependent on the choice of ELISA system" BMC Cancer, 6(1):207, 2006). The authors did not consider that the differences between the assays may be due to the detection (or lack of detection) of the specific osteopontin fragments that correlate with disease presence, progression and prognosis.

Therefore, what is needed are reagents and methods that will specifically detect osteopontin fragments and distinguish them from each other and from the full-length protein.

SUMMARY OF THE INVENTION

The present invention relates to reagents and methods for the detection of osteopontin fragments and distinguishing them from each other and from the full-length osteopontin protein. The present invention also relates to assays for the determination of the presence of osteopontin fragments in samples obtained from subjects and, further, the correlation of osteopontin fragment levels with disease detection, progression and prognosis.

In one embodiment, the present invention relates to an assay designed, for example, to detect osteopontin fragments in a sample. The sample may be from a subject or may be a freshly obtained or a stored sample (e.g., a frozen sample). The sample may be, for example, serum, plasma, blood, breast milk, sputum, semen, wound secretions, tears, mucous or any other bodily fluid or secretion known or suspected of comprising osteopontin. The sample may also be a tissue or tissue homogenate. The subject may be any living organism known to produce osteopontin and/or osteopontin fragments or suspected of producing osteopontin and/or osteopontin fragments. For example, the subject may be any mammal including humans. Additionally, the sample may be derived from in vitro sources such as synthesized peptides and peptide fragments or peptides and fragments made recombinantly. Such synthetic or recombinantly made peptides and fragments may be used to, for example, calibrate an assay, serve as positive and/or negative controls or test the efficacy of new antibodies for the ability to recognize and bind osteopontin and osteopontin fragments.

The present invention is not limited to any particular assay format for the detection of osteopontin fragments. Any assay capable of detecting osteopontin fragments and distinguishing them from full-length osteopontin is within the scope of the present invention. By way of example, in one embodiment, the present invention contemplates an assay comprising capturing an osteopontin fragment with a capture antibody which binds to a first epitope of the osteopontin fragment, detecting the captured osteopontin fragment with an antibody that binds specifically to a second epitope of the osteopontin fragment and, determining that the peptide is a fragment by detecting a lack of binding by a determining antibody that binds specifically to a third epitope of osteopontin, as compared to a suitable control. The use of three antibodies, as opposed to an assay using just two antibodies, increases accuracy and decreases erroneous results by, for example, decreasing the occurrence of false positives.

In another embodiment of the present invention, an assay is contemplated comprising capturing an osteopontin fragment with a capture antibody which binds specifically to either the N-terminus or C-terminus of the osteopontin fragment and determining that the peptide is a fragment by detecting a lack of binding by a determining antibody that binds specifically to the C-terminus of the osteopontin protein if an antibody specific for the N-terminus was used as the capture antibody or by detecting a lack of binding by a determining antibody that binds specifically to the N-terminus of the osteopontin protein if an antibody specific for the C-terminus was used as the capture antibody, as compared to a suitable control.

Furthermore, the present invention relates to antibodies with specificity to osteopontin fragments. Although the present invention is not limited to any specific antibody or antibodies, the present invention relates, for example, to antibodies designated 2C5, 2H9, 2F10, 2E11 and 1F11, which have been shown to have specific reactivity with the N-terminal fragment of OPN or the C-terminal fragment of OPN, as described in detail, infra.

Other embodiments of the present invention will become evident to one practiced in the art based on the teachings as given in the Detailed Description of the Invention and the Exemplification sections of this document.

DETAILED DESCRIPTION OF THE INVENTION

Figure 1:
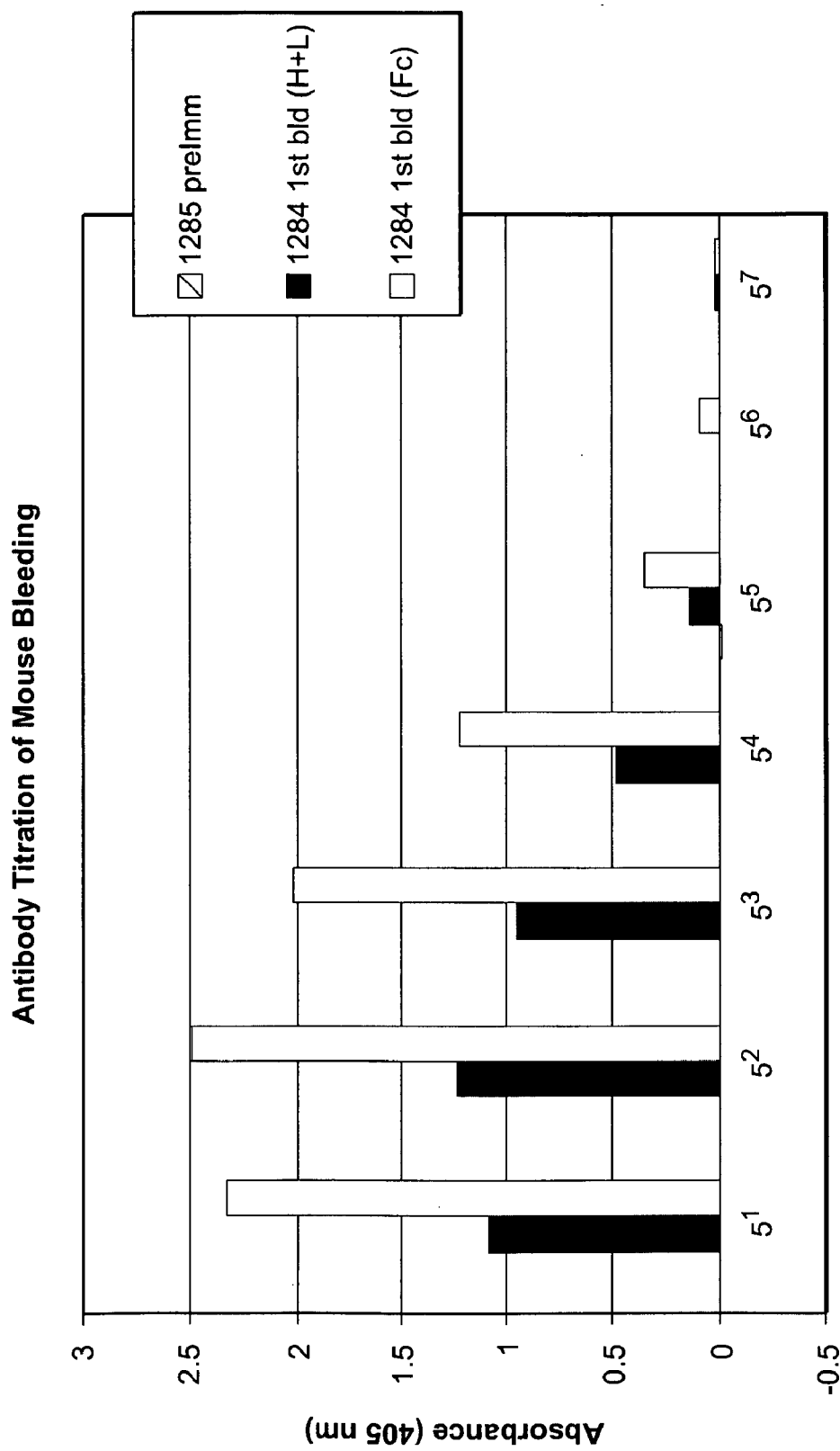
FIG. 1 shows the antibody titration of various mouse bleeds. 1285 preImm: Blood serum from OPN-null mouse strain 1285 before the mouse was immunized with h-FL OPN. 1284 $1^{st}$ bld (H+L): Blood serum collected from mouse strain 1284 after immunizing five times with h-FL OPN and with the second antibody HRP-conjugated goat anti-mouse IgG+IgM heavy and light chain used in this assay. 1284 $1^{st}$ bld (Fc): Same as 1284 $1^{st}$ bld except the second antibody was HRP-conjugated goat anti-mouse IgG specific for the antibody's Fc portion.

The present invention relates to reagents and methods for the detection of osteopontin fragments and distinguishing them from each other and from the full-length osteopontin protein. The present invention also relates to assays for the determination of the presence of osteopontin fragments in samples obtained from subjects and, further, the correlation of osteopontin fragment levels fragment levels with disease detection, progression and prognosis.

As defined herein, the term "fragments" refer to any peptide having the full-length osteopontin sequence less one or more amino acids including, but not limited to, splice variants, mutations, deletions, substitutions, etc.

As defined herein, the terms "N-terminal" and "N-terminus" of the osteopontin protein fragment refers to, for example, approximately amino acids 1-166 of the osteopontin protein when cleaved by matrix metalloproteinases, or portion thereof. Also, as defined herein, the terms "N-terminal" and "N-terminus" of the osteopontin protein fragment refers to, for example, approximately amino acids 1-168 of the osteopontin protein when cleaved by thrombin, or portion thereof. Those practiced in the art will recognize that other proteases will cleave osteopontin at different cleavage sites thereby resulting in "N-terminal" and "N-terminus" fragments of varying sizes. Additionally, osteopontin fragments may be made synthetically and may include N-terminal fragments of various sizes.

As defined herein, the terms "C-terminal" and "C-terminus" of the osteopontin protein fragment refers to, for example, approximately amino acids 167-314 of the osteopontin protein when cleaved by matrix metalloproteinases, or portion thereof. Also, as defined herein, the terms "C-terminal" and "C-terminus" of the osteopontin protein fragment refers to, for example, approximately amino acids 169-314 of the osteopontin protein when cleaved by thrombin, or portion thereof. Those practiced in the art will recognize that other proteases will cleave osteopontin at different cleavage sites thereby resulting in "C-terminal" and "C-terminus" fragments of varying sizes. Additionally, osteopontin fragments may be made synthetically and may include C-terminal fragments of various sizes.

As defined herein, the term "capture antibody" refers to an antibody that is capable of being removably or irremovable attached to a solid surface and is capable of binding to a target epitope on a target molecule (e.g., a peptide and, more preferably, an osteopontin peptide or fragment thereof).

As defined herein, the term "detecting antibody" refers to an antibody that is capable of binding to a target epitope on the target molecule preferably after the target molecule has been captured by a capturing antibody. Also, preferably, the detecting antibody is specific for an epitope that is different than the epitope recognized by the capture antibody.

As defined herein, the term "determining antibody" refers to an antibody that is capable of binding to an epitope on the same target molecule as the capturing and detecting antibodies, wherein said epitope is not recognized by either the capture or detecting antibody. In one embodiment of the invention, the target molecule is an osteopontin fragment and the target molecule for the determining antibody is located on the portion of the osteopontin fragment that has not been captured by the capture molecule.

As defined herein, the term "binds specifically" or similar terms, when used in the context of an antibody binding a target epitope, refers to the antibody having specificity for the target epitope (as opposed to other epitopes). The specificity need not be 100%. In one embodiment, the specificity is about 75% or greater (i.e., 75% specificity for the epitope). This means that about 75% of the antibodies that bind to an epitope will bind to the target epitope and about 25% of the antibodies will bind non-specifically. In another embodiment, the specificity is about 90% or greater.

In one embodiment, the present invention relates to an assay designed, for example, to detect osteopontin fragments in a sample. The sample may be from a subject. The sample may comprise, for example, serum, plasma, blood, breast milk, sputum, semen, wound secretions, tears, urine, mucous or any other bodily fluid or secretion. Additionally, the sample may be a tissue sample. The subject may be any living organism known or suspected of producing osteopontin and/or osteopontin fragments. For example, the subject may be any mammal including humans. Additionally, the sample may be derived from in vitro sources such as synthesized peptides and peptide fragments or peptides and fragments made recombinantly. Such synthetic or recombinantly made peptides and fragments may be used to, for example, calibrate an assay, serve as positive and/or negative controls or test the efficacy of new antibodies for the ability to recognize and bind osteopontin and osteopontin fragments.

The present invention is not limited to any particular assay format for the detection of osteopontin fragments. Any assay capable of detecting osteopontin fragments and distinguishing them from full-length osteopontin is within the scope of the present invention. By way of example, in one embodiment, the present invention contemplates an assay comprising capturing an osteopontin fragment with a capture antibody which binds to a first epitope of the osteopontin fragment, detecting the captured osteopontin fragment with an antibody that binds specifically to a second epitope of the osteopontin fragment and, determining that the peptide is a fragment by detecting a lack of binding by a determining antibody that binds specifically to a third epitope of the osteopontin fragment.

The present invention is not limited by the antibodies used so long as they meet the criteria of binding specifically to different epitopes of the osteopontin protein, as defined above. For example, in one embodiment, the capture and detecting antibodies bind to different epitopes on the N-terminus of the osteopontin protein and the determining antibody binds specifically to an epitope on the C-terminus of the osteopontin protein. In another embodiment, the capture and detecting antibodies bind to different epitopes on the C-terminus of the osteopontin protein and the determining antibody binds specifically to an epitope on the N-terminus of the osteopontin protein. In another embodiment, the capture and detecting antibodies bind to the same or similar epitope but are used in sub-saturating concentrations so that the epitope is not saturated by the capture antibody before the introduction of the detecting antibody. In one embodiment, the antibodies are monoclonal, polyclonal or a mixture of monoclonal and polyclonal antibodies.

In a preferred embodiment, the antibodies of the present invention are monoclonal antibodies designated were submitted to the ATCC (Manassas, Va.) on Nov. 2, 2010 for deposit as required under 37 CFR 1.809(c)(d) and are monoclonal antibodies 2C5 (produced by a hybridoma deposited as ATCC Accession No. PTA-11447), 2H9 (produced by a hybridoma deposited as ATCC Accession No. PTA-11446), 2F10 (produced by a hybridoma deposited as ATCC Accession No. PTA-11450), 2E11 (produced by a hybridoma deposited as ATCC Accession No. PTA-11449) and 1F11 (produced by a hybridoma deposited as ATCC Accession No. PTA-11448), the production of which is described in the Exemplification section, infra. The antibodies designated 2C5, 2H9 and 2F10 bind specifically to different epitopes of the N-terminus of the osteopontin protein. The antibodies designated 2E11 and 1F11 bind specifically to different epitopes of the C-terminus of the osteopontin protein.

The present invention is not limited to any particular assay format. Many different assay formats exist which may be useful in the present invention. For example, the assay format may be that of an Enzyme Linked ImmunoSorbent Assay (ELISA). ELISAs are designed for detecting and quantitating substances such as peptides, proteins, antibodies and hormones. Other names, such as Enzyme ImmunoAssay (EIA), are also used to describe the same or similar process. In an ELISA, an antigen must be immobilized to a solid surface. The solid surface may be, for example, the surface of a Petri dish or a micro-carrier bead. The antigen is then complexed with an antibody that is linked to an enzyme. Detection is accomplished by incubating this enzyme-complex with a substrate that produces a detectable product. The most crucial element of the detection strategy is a highly specific antibody-antigen interaction.

Most commonly, ELISAs are performed in 96-well (or 384-well) polystyrene plates, which will passively bind antibodies and proteins. It is this binding and immobilization of reagents that makes ELISAs so easy to design and perform, as first described by Eva Engvall, et al. (Enzyme-linked immunosorbent assay. II. Quantitative assay of protein antigen, immunoglobulin G, by means of enzyme-labelled antigen and antibody-coated tubes. Biochim Biophys Acta, 251(3): 427-434, 1971). Having the reactants of the ELISA immobilized to the microplate surface makes it easy to separate bound from unbound material during the assay. This ability to wash away nonspecifically bound materials makes the ELISA a powerful tool for measuring specific analytes within a crude preparation.

A detection enzyme may be linked directly to the primary antibody or introduced through a secondary antibody that recognizes the primary antibody. It may also be linked to a protein such as, for example, streptavidin if the primary antibody is biotin labeled. The most commonly used enzymes are horseradish peroxidase (HRP) and alkaline phosphatase (AP). Other enzymes have been used as well. These include, for example, β-galactosidase, acetylcholinesterase and catalase. A large selection of substrates is available for performing the ELISA with an HRP or AP conjugate. For HRP, Promega's (Madison, Wis.) TMB substrate and Sigma's (St. Louis, Mo.) CPS Chemiluminescent Peroxidase Substrate, are just two examples known in the art. Chromatographic and chemiluminescent substrates, among others, are also available for AP and are well known in the art. The present invention is not limited by the choice of detection enzyme or substrate as long as they are compatible with each other. The choice of substrate depends upon the necessary sensitivity level of the detection and the instrumentation available for detection (spectrophotometer, fluorometer or luminometer). ELISA assays are well known in the art. In addition to the above formats they may be preformed in microtiter plates, in microarrays, in assay tubes (e.g., eppendorf tubes) or on micro-carrier suspensions, etc. ELISA assays may be read manually, with plate readers or the assay may be automated by the use of, for example, robotics. Other assays are also useful in the present invention. For example, radioimmunoassays (RIA) may be used. These assays are also well known in the art (see, e.g., Boden and Chey, "Preparation and specificity of antiserum to synthetic secretin and its use in a radioimmunoassay (RIA)," Endocrinology, 92(6):1617-1624, 1973).

Still other assay formats exist that may be used with the present invention. For example, immuno-affinity chromatography may be used. In one example, the capture antibody is bound to the column matrix. A sample is passed through the column and the column washed. A detecting antibody is then passed over the column and washed. The determining antibody is then passed over the column and washed. The presence of osteopontin fragments can then be determined based on the amount of detecting and determining antibodies recovered or by labeling as discussed both supra and infra. Those skilled in the art will know of other suitable assay systems for use with the present invention.

The antibodies bound to the suspected osteopontin fragment may be detected by any means known in the art. The present invention is not limited to any particular detection means for detecting bound or unbound antibodies. In addition to the means discussed above, biotin-avidin systems are known in the art and can be used with the present invention. Chromatographic, chemiluminescent and fluorescent detection systems are also known in the art and can be used with the present invention. Detection systems may be either direct (with the detection molecule conjugated directly to the primary antibody, i.e., the capture detection or determining antibody of the present invention) or indirect (with the detection molecule conjugated to a secondary antibody that has specificity for the primary antibody).

The reagents and methods of the present invention are useful in the detection of various diseases and determining the progression and prognosis of those diseases. The present invention is not limited to any particular disease so long as osteopontin fragments are known or suspected of being an indicator of disease presence, progression and/or prognosis. Some diseases in which the generation of osteopontin fragments is known or suspected of being an indicator of disease presence, progression and/or prognosis are breast cancer, prostate cancer, and lung cancer. Determination of the progress of a disease may be accomplished, for example, by testing for the presence of osteopontin fragments over time with the methods of the present invention. Based on the how the disease has progressed, as determined by the methods of the present invention, one skilled In the art will be able to generate a prognosis of the disease.

More specifically, the present invention also relates to reagents and methods for the detection of cancer in a subject as well as for monitoring the progression and prognosis of the disease. In one embodiment, the present invention detects cancer by measuring the level of osteopontin fragments in a bodily fluid derived from the subject using the reagents and methods of the present invention. The level of osteopontin may be determined over time to monitor the progression of the disease (either as it increases in severity or as it responds to treatment(s)) and determine the prognosis of the disease based on changes in the level of osteopontin fragments and/or a change in the fragment sizes in the subject sample over time and/or as compared to historic data. The Exemplification section of the present application, below, provides details of non-limiting examples of how the reagents and methods of the present invention may be used for detection, monitoring the progression and determining the prognosis of subjects that have or are suspected of having diseases associated with the generation of osteopontin fragments.

EXEMPLIFICATION

Materials and Methods

Production of Monoclonal Antibodies. The following proteins were provided by Dr. Lucy Liaw (Maine Medical Center Research Institute, Portland, Me.): h-FL OPN (*E. coli* expression), GSTOPN(OPN with GST tag cleaved) (*E. coli* expression), m-FL OPN (*E. coli* expression), N-terminal OPN (*E. coli* expression) and C-terminal OPN (*E. coli* expression). Control His-tagged swine viral protein (+21×His-tag) was generously provided by Idexx (Portland, Me.).

All centrifugations were performed at 1,000 rpm for 10 minutes unless noted otherwise. All media and buffers used were at room temperature unless noted otherwise. The entire experimental procedure was carried out at room temperature. Incubation was performed in a 37° C. incubator filled with 5% $CO_2$.

Immunization. Pre-immunization blood was collected the retro-orbitally from an 11-month old female C57 BL OPN-null mouse (1284: OPN−/−) provided by Dr. Lucy Liaw. Immunizations were started at Day 0 by a subcutaneous injection of 100 µg of h-FL OPN suspended in 500 µl of CFA (Complete Freud's Adjuvant; Sigma, St. Louis, Mo.: Cat. No. F5881), followed by subsequent injections each with 50 µg of h-FL OPN in 500 µl of IFA (Incomplete Freud's Adjuvant; Sigma Cat. No. F5506) on Day 13, Day 33, Day 45 and Day 161. At Day 170 the mouse was bled and the antibody titer was measured by ELISA (see, below). Twenty-two days after the bleeding test a final injection was administered with 30 µg h-FL OPN in 150 µl IFA in the peritoneal cavity and with 20 µg in 100 µl IFA subcutaneously. Four days later the mouse was bled, sacrificed and the spleen collected (Table 1).

TABLE 1

Mouse Identification and Immunization Steps

| Mouse Strain | Mouse ID# | DOB | Sex | Parents |
|---|---|---|---|---|
| C57 BL OPN-null | 1284 | Apr. 05, 2004 | Female | 994 X 1078 |

| Day | Immunization Route | Comments: |
|---|---|---|
| 0 | SC | Pre-immunization bleed, 100 µg purified recombinant FL human OPN with Complete Freud's Adjuvant |
| 13 | SC | 50 µg purified recombinant FL human OPN with Incomplete Freud's Adjuvant |
| 33 | SC | 50 µg purified recombinant FL human OPN with Incomplete Freud's Adjuvant |
| 45 | SC | 50 µg purified recombinant FL human OPN with Incomplete Freud's Adjuvant |
| 161 | SC | 50 µg purified recombinant FL human OPN with Incomplete Freud's Adjuvant |
| 170 | | Bleed (retro-orbital) |
| 192 | IP & SC | 50 µg purified recombinant FL human OPN with Incomplete Freud's Adjuvant |

TABLE 1-continued

Mouse Identification and Immunization Steps

| 197 | Bleed (retro-orbital), spleen collected, cell fusion started |

Antibody Titration Using ELISA. After five rounds of immunization 0.1 ml blood was collected from mouse eyes in order to determine the OPN antibody production level in the serum. A 96-well microtiter plate (BD Biosciences, Bedford, Mass.: Cat. No. BD353279) was coated with 50 ng/ml (100 μl/well) of purified h-FL OPN and incubated at 4° C. overnight. Subsequently, the plate was blocked with 3% nonfat dry milk in PBS-T (Phosphate Buffer Saline-Tween; PBS pH 7.3, 0.05% Tween 20) at room temperature for 2 hours. The sample serum was then loaded to the first column of the plate at 1 ul to 99 μl of 3% nonfat dry milk in PBS-T, followed by serial 5-fold dilutions. After incubation at 37° C. for 1 hour the plate was washed 3× with PBS-T and incubated at 37° C. for 2 hours with a combination of two separate secondary antibodies at 100 μl/well. One of the secondary antibodies was a 1:5000 diluted Peroxidase (HRP)-conjugated Goat Anti-Mouse IgG, $Fc_\gamma$ fragment specific (Jackson ImmunoResearch Laboratories, West Grove, Pa.: Cat. No. 66350) and the other was a 1:5000 diluted Peroxidase (HRP)-conjugated AffiniPure Goat Anti-Mouse IgG+IgM (H+L) (Jackson ImmunoResearch Laboratories; Cat. No. 66877). Use of the two secondary antibodies allowed the detection of both IgG and IgM types of antibodies against OPN.

Finally, the plate was washed 4 times with PBS-T, followed by incubation with 100 μl/well of TMB (Tetramethyl benzidine) at room temperature in darkness for 15 minutes. The chromogenic reaction was stopped by 100 μl/well of 1 M HCl. The amount of the antibodies against h-FL OPN was determined by reading the plate at 405 nm using an automated microplate reader (Bio-Tek Instruments).

Fusion of Splenocytes and Myeloma Cells. The hybridoma cells producing antibodies against OPN were generated by fusing splenocytes with myeloma cells according to a standard protocol developed by Kohler and Milstein (Kohler G, Milstein, C, 1975). The FO myeloma cells were a gift from Hatim Chraibi (Maine Biotechnology Services, Portland, Me.; see, also ATCC, Bethesda, Md.: Cat. No. CRL-1646; de StGroth and Scheidegger, J Immunol Methods, 35(1-2):1-21, 1980). These cells were harvested and washed in mid-log phase with a cell concentration of $9.5 \times 10^5$ cells/ml at the time of fusion.

The spleen from the immunized mouse was first removed and washed 3 times with 2 ml of serum-free DMEM/F12 (Mediatech, Inc, Herndon, Va.: Cat. No. 10-090-CV). It was then placed in a Petri dish with a few drops of serum-free DMEM/F12. After smashing the spleen between two fine sterile screens the splenocytes were separated and collected by rinsing the Petri dish and the screens 3 times with 5 ml of serum-free DMEM/F12. These cells were then centrifuged and resuspended in 4.5 ml of cold red blood cell lysing buffer (17 mM tris-HCl, pH 7.2, 0.144 M $NH_4Cl$), and sit at room temperature for 5 minutes. After addition of 10 ml of cold DMEM/F12 they were centrifuged again and resuspended in 20 ml serum-free DMEM/F12. A total of $8.2 \times 10^7$ cells collected.

The cell fusion was achieved by combining these two cell populations at a 5:1 (splenocyte:myeloma) ratio. Following washing and centrifugation, 2 ml of pre-warmed 50% PEG (Sigma, St. Louis, Mo.: Cat. No. 72K2300) was added to the cell pellet in a drop by drop fashion over 1 minute period while swirling the tubes gently and the suspension was stirred with a 1-ml glass pipette for an additional minute. Subsequently, 5 ml of serum-free DMEM/F12 were added in the same fashion over a 2 minute period immediately followed by the addition of another 5 ml of serum-free DMEM/F12. The cell suspension was then allowed to sit at room temperature for 3 minutes before receiving 40 ml of HT (hypoxanthine and thymidine) medium (DMEM/F12, 10% FBS, Omega Scientific: Cat. No. FB-02; 1% penicillin/streptomycin, Cambrex: Cat. No. 17-602E; 1% L-Glutamine, Cambrex: Cat. No. 17-605E; 1×HT supplement, Gibco: Cat. No. 11067-030; 10% NCTC, Cambrex: Cat. No. 12-923E; 0.01% Insulin-Transferrin-Selenium, Gibco: Cat. No. 41400-045) to achieve a total volume of 50 ml. The cells were centrifuged at 700 rpm for 7 minutes, washed and resuspended in 40 ml HT medium to achieve a final concentration of $7 \times 10^5$ myeloma cells/ml. The fused cells were then incubated with culture flasks in an upright position at 37° C. and 5% $CO_2$ for 1.5 hours with 1.6 ml 50× Aminopterin added at the end of incubation. Finally, the cell suspension was transferred to 96-well tissue culture plates (BD Biosciences: Cat. No. 353072) at 100 μl/well and incubated at 37° C. for 10 days.

Screening of Hybridoma culture Supernatants by ELISA. The hybridoma culture supernatants were initially screened with 100 ng/ml h-FL OPN using Peroxidase (HRP)-conjugated goat anti-mouse IgG+IgM (H+L) as the secondary antibody. In the follow-up screenings GSTOPN (OPN with GST tag cleaved), a recombinant human OPN without His-tag, was used in addition to h-FL OPN as the positive antigens. These screenings also included control His tagged swine viral protein and 1×PBS as negative controls along with Peroxidase (HRP)-conjugated goat anti-mouse IgG, $Fc_\gamma$ specific as the secondary antibody.

The ELISA was conducted essentially as described above. The 96-well microtiter plate was coated with 50-100 ng/ml of antigen and a 1:5000 diluted HRP-conjugated goat anti-mouse antibody was used as the secondary antibody.

If a well was tested positive with both h-FL OPN and GST as antigen and with HRP-conjugated Goat anti-mouse IgG, $Fc_\gamma$ as secondary antibody the corresponding hybridoma culture was expanded and retested for three times. Three primary hybridoma cultures—1284:4E8, 1284:2B11, and 1284:3G11—were selected for subcloning by limiting dilution 18 days after fusion. The rest of the positive primary hybridoma cell lines were frozen and stored in liquid Nitrogen.

Rescue the Low Antibody Activity Hybridomas. ELISA testing showed that Hybridomas 1284:4F8 and 1284:1H4 had low antibody activities. In an attempt to boost their antibody yield a rescue method based on serial limiting dilution was employed to isolate and enrich the hybridoma cells secreting anti-OPN antibodies. Initially, the cells were grown to log phase, counted, diluted with HT medium to 5000 cells/100 μl and grown in a 96-well plate at 37° C. for 2-3 days. Subsequently, the hybridoma supernatants were screened with ELISA and the cells that produced strong signals (rated "++" or higher as in Table 2) were collected and subjected to the above steps at serially increasing densities, i.e., at 500, 100 and 10 cells/100 μl. In Table 2 a list of polyclonal primary hybridomas secreting anti-OPN antibodies developed from OPN immunized mice 1284 and 1283. The number of "+" symbols is an indicator of antibody activity level. "Y" indicates the location of an antibody-binding site (i.e., an epitope) on the OPN fragment. The antibody activities for 1284:4F8 and 1284:1H4 were the results after rescue. Finally, the cell cultures were expanded and stored in liquid nitrogen.

TABLE 2

ELISA Screening of Primary Hybridomas Positive for anti-OPN antibodies.

| Hybridoma | Antibody activities (against h-FL OPN) | N - Terminal OPN specificity | C - Terminal OPN specificity |
|---|---|---|---|
| 1283: 1C12 | +++ | | |
| 1283: 2G8 | +++ | Y | |
| 1284: 4E8 | +++ | Y | |
| 1284: 2B11 | +++ | | Y |
| 1284: 3G11 | +++ | Y | |
| 1284: 2C10 | +++ | | Y |
| 1284: 4F8 | +++ | Y | |
| 1284: 1H4 | ++ | | |

+++: $A_{405\,nm}$ = 0.8-2.0,
++: $A_{405\,nm}$ = 0.5-0.8,
+: $A_{405\,nm}$ < 0.5

Subcloning. The two hybridoma cell lines, 1283:1C12 and 1283:2G8, were generated previously in our laboratory. These two cell lines produced mouse polyclonal antibodies against h-FL OPN. After being thawed at 37° C. they were tested for their antibody-producing activities as described above.

A total of five cell lines, 1283:1C12, 1283:2G8, 1284:4E8, 1284:2B11 and 1284:3G11, were grown to log phase before being harvested, counted and diluted with HT medium containing 10% hybridoma cloning factor (BioVeris Corp, Gaithersburg, Md.: Cat. No: 210001) to 0.5-1 cell/200 µl. The diluted cells were then plated at 0.5-1 cell/well and observed for colony growth from a single clone after a 3-day incubation period. At 10-14 days into incubation positive subclones were identified by ELISA and then expanded and frozen in liquid nitrogen. The corresponding cell supernatants were stored at −20° C. Three of the five cell lines, 1283:1C12, 1283:2G8, and 1284:4E8, were subjected to this subcloning procedure for 2-3 times until a true monoclone from each cell line was identified.

Production of Ascites Fluid. The strain of mouse used in the ascites production was 6- to 8-week old OPN heterozygotes with $H-2^{b/d}$ MHC molecules, which were offspring from a cross between the C57/BL $H-2^b$ and the Balb/c $H-2^d$. These heterozyzotes were used to produce acsites fluid because the anti-OPN hybridoma cells were generated by fusing the $OPN^{-/-}$ C57/BL mouse splenocytes with Balb/C mouse FO cells. These hybridoma cells, carrying MMC $H-2^{b/d}$ molecules, could only grow in mice with the same MHC background.

F1 hybrid offsprings of the C57/BL and Balb/c mice were first primed with an intraperitoneal injection of 500 µl of IFA. Seven to ten days later $5\times10^5$-$5\times10^6$ washed hybridoma cells were injected into the peritoneum. When ascites was evident the mice were sacrificed for ascites fluid collection. Ascites production was approved and supervised by the Maine Medical Research Institutional Animal Care Use Committee.

Purification of Ascite Fluid. After the ascites fluid was collected (see, above), the lipids and cell debris were removed by centrifugation at 14000 g for 15 minutes. The purified ascites fluid sample was diluted by adding 5 volumes of the binding buffer (20 mM sodium phosphate buffer, pH 7.0).

Preparation of Protein G Column. The Protein G Resin Slurry (Immobilized Protein G, Pierce Cat. No. 20398) was poured into a gravity-flow column (a gift from the Foundation of Blood Research, Portland, Me.) to a gel bed volume of 1 ml for each ascite sample. The columns were equilibrated by adding 5 ml of the binding buffer and the solution was allowed to drain through the column.

Purification of the MAbs. After the diluted samples were loaded and cycled through the column for three times. The column was washed with 5 ml of binding buffer to remove any unbound proteins and the wash was collected in 1-ml aliquots (labeled as protein G Flow Thru). The antibodies were eluted with 5 ml of elute buffer (0.1 M Glycine-HCL, pH 2.7), collected in 1-ml fractions and immediately adjusted to physiologic pH by adding neutralization buffer (1 M Tris-HCL, pH 8.0). The protein G column was re-equilibrated with 5 ml binding buffer.

The quantities of the proteins were determined using a DC protein assay kit (Bio-Rad Laboratories, Hercules, Calif.: Cat. No. 500-0116). On average, 1-4 mg of antibodies were produced from 1 ml of ascite fluid. Purities were assessed by SDS-PAGE and coomassie blue staining Briefly, 10 µg/lane of reduced antibody samples were resolved on a 12.5% polyacrylamide gel following the procedure given above. The gel was then stained in Coomassie blue (0.025% Coomassie brilliant blue 8250, 40% (v/v) methanol, 7% (v/v) acetic acid) at room temperature overnight, followed by destaining with destain solution I (40% (v/v) methanol, 7% (v/v) acetic acid) for 1 hour and with destain solution II (5% (v/v) methanol, 7% (v/v) acetic acid).

Dialysis. The eluted antibody fractions were loaded into a 12,000-14,000 MWCO (molecular weight cut-off) Spectra/Por molecularporous membrane dialysis tubing (Spectrum, VWR) and dialyzed in >100 volumes of PBS buffer (pH 7.3) at 4° C. for 36 hours. The dialysis buffer was changed 3 times during dialysis.

Biotin-NHS Biotinylation of Antibodies (1F11, 2F10 and 1E3). Sulfo-NHS-LC-Biotin [sulfosuccinimidyl-6-(biotinamido) hexanoate] (MW 556.59, Pierce) was prepared at 10 mg/ml in PBS and added to dialyzed MAbs 1F11, 2F10 and 1E3 at a ratio of 186 µg, 148 µg and 150 µg of biotin per milligram of antibody, respectively. 1E3, a monoclonal antibody against platelets activation antigen CD62-P (P-selectin) was used as a control.

The mixtures were incubated at room temperature for 1 hour before being dialyzed extensively against PBS to remove uncoupled biotin. The quantities of the biotinylated proteins were then determined using a DC protein assay kit (Bio-Rad Laboratories, Hercules, Calif.).

Characterization of Monoclonal Antibodies (MAbs)

Isotyping of MAbs 2E11, 2C5, 2H9, 1F11 and 2F10. The isotypes of 2E11, 2C5, 2H9, 1F11 and 2F10 were determined with the IsoStrip Mouse Monoclonal Antibody Isotyping Kit (Roche, Indianapolis, Ind.: Cat. No. 1493027), following manufacturer's instructions. Briefly, 150 µl of a neat (unpurified) antibody supernatant sample was added to a development tube (included in the kit) and briefly agitated to resuspend the colored latex particles completely. An isotyping strip was then inserted into the development tube with the black end at the bottom and incubated for 5-10 minutes. The appearance of a blue band in the class or subclass section of the strip, as well as in the κ or λ section, was an indication of the antibody's class or subclass and light-chain composition.

Indirect ELISA. A 96-well flat bottom ELISA plate was coated with 100 µl (200 ng/ml in PBS pH 8.0) of antigens at 4° C. overnight. Depending on the purpose of the experiment, different antigens were used:

For antibody specificity test, the wells were coated with h-FL OPN, GSTOPN, control His-tagged swine viral protein and 1×PBS (pH 7.3), respectively, with the latter two as negative controls.

For antibody species cross-reaction test, the wells were coated with h-FL OPN and m-FL OPN, respectively.

For antibody epitope mapping test, the wells were coated with h-FL OPN (62 KDa) and its N- and C-terminal fragments (40 KDa for N-terminal and 25 KDa for C-terminal), respectively.

The rest of the ELISA procedure was carried out as described above except after blocking supernatants of the hybridoma culture fluids or purified ascite fluids were added to each well with or without dilution followed by 2-hour incubation at 37° C.

SDS-PAGE and Western Blot Analysis. The sodium dodecyl sulfate-polyacrylamide gel eletrophoresis (SDS-PAGE) was performed with a Mini-PROTEAN Gel Electrophoresis Unit (Bio-Rad Laboratories, Hercules, Calif.). Protein samples were diluted appropriately and boiled for 5 minutes in the sample buffer (63 nM Tris, 2% SDS, 0.01% bromphenol blue, 5% β-mercaptoethanol). For samples of h-FL OPN, m-FL OPN, N-terminal OPN and C-terminal OPN, 20 ng of protein were loaded in each lane of a 12.5% polyacrylamide gel. For tissue lysates, 10-20 µg/lane of proteins were used. Proteins were separated with 100 V constant voltage using the buffer system of Laemmli (Laemmli, U. K. 1970. Cleavage of structural proteins during the assembly of the head of bacteriophage T4. Nature 227:680-685; Biorad Instruction Manual) for approximately 1-2 hours. The running buffer consisted of 25 nM Tris base, 192 mM glycine, 0.1% SDS, pH 8.8.

The separated proteins on the gel were transferred to a polyvinylidene difluoride (PVDF) membrane with the Mini-PROTEAN Gel Electrophoresis Unit (Bio-Rad Laboratories) running at 350 mA for 1-2 hours. The transfer buffer consisted of 25 mM Tris, 192 mM Glycine and 0.1% SDS, pH 8.3 (Biorad Instruction Manual).

Nonspecific binding was blocked with 5% nonfat dry milk in TBS-T buffer (10 nM Tris Base, pH 8.0, 150 nM NaCl, and 0.05% Tween 20) at room temperature for 1 hour. The membrane was then incubated in a neat MAb hybridoma culture supernatant or a diluted purified MAb (1:500) in 5% milk TBS-T. After overnight incubation at 4° C., the membrane was washed 5 times with TBS-T. The secondary antibody, HRP-conjugated goat anti-mouse IgG, $Fc_7$, (1:10,000) in 5% milk TBS-T (Tris-Buffer Saline, Tween), was then added to the membrane. After 1-hour incubation and 5 washings with TBS-T, the OPN bands were visualized using a chromogenic TMB substrate (provided by Binax, Scarborough, Me.) and a CN/DAB substrate Kit (Pierce, Rockford, Ill.: Cat. No. 34000) with a 10-minute incubation in darkness. The reaction was stopped by rinsing the membrane in distilled water.

Alternatively, an ECL Western blotting detection reagent (Amersham, Chicago, Ill.: Cat. No. RPN2108) was used and the Western blot results developed on a Kodak X-ray film. Prestained molecular weight standards (Bio-Rad, Hercules, Calif.: Cat. No. 161-0305) were used to estimate protein sizes.

Indirect Competition ELISA. To compare epitope specificity, unlabeled anti-OPN MAbs were used to compete with biotinylated 1F11 and 2F10 for binding to specific OPN epitopes. Briefly, a 96-well plate was coated with 200 ng/ml (100 µl/well) h-FL OPN and blocked with 3% non-fat dry milk with PBST for 1 hour at 37° C. Subsequently, 100 µl/well of PBS+milk (blank, negative control), UCD/PR (negative control) and monoclonal antibodies 2E11, 2C5, 2H9, 1F11 and 2F10 culture supernatants were added, followed by incubation at 37° C. for 1-2 hours. After the plate was washed with 3×PBS-T, 100 µl/well 1:500 diluted biotinylated 1F11 (0.66 µg/ml) or 1:500 diluted biotinylated 2F10 (1.43 µg/ml) were added and incubated at 37° C. for 1 hour. Following wash with 3×PBS-T, the plate was incubated with 100 µl/well 1:1000 diluted HRP-conjugated Streptavidin (Jackson ImmunoResearch Laboratories, West Grove, Pa. Cat. No. 55889) for 1 hour at 37° C. The rest of the ELISA steps were performed as described above Tissue Extracts. Kidney and skull tissue extractions from rats and mice were used to assess the reactivity of the MAbs with native OPN. The rat tissue extracts were provided by Dr. Volkhard Lindner (Maine Medical Research Institute, Portland, Me.). Extracts from wild-type, OPN-deficient mice and OPN heterozygotes (described above) were used as positive and negative controls for Western blots, respectively. Briefly, after the mice were sacrificed, the skulls and kidneys were removed and immediately frozen in liquid nitrogen. The frozen tissue was manually ground into powder and suspended in lysis buffer (0.05 M Tris pH 7.6, 1% SDS, 0.001 M PMSF, 10 µg/ml leupeptin, 10 µg/ml aprotinin) and sonicated. The suspension was centrifuged at 15,000 g for 5 minutes and the supernatant was retained. The quantities of the extract proteins were determined using a DC protein assay kit. Western blots were performed as described above.

Immunohistochemistry. A 15-day old wild-type mouse embryo was fixed in periodate-lysine-paraformaldehyde (PLP) at 4° C. for 24-48 hours, cryoprotected in 20% sucrose in PBS at 4° C. overnight and then frozen in OCT compound (a low-temperature embedding medium for cryosectioning techniques, Leica, Bannockburn, Ill.). The tissue sections (5 µm in thickness) were prepared with a Cryocut 1800 tissue sectioner (Leica), and stored at −70° C. until use.

Before immuno-detection, the slides were dried at 60° C. for 20 minutes and rinsed in tap water to wash off the tissue embedded compound OCT, followed by baking at 60° C. for another 20-30 minutes and rinsing in PBS. Antigens were retrieved from the cells by steam boiling the tissue sections in citrate buffer (pH 6.0, 0.01 M citric acid monohydrate, 0.01 M Sodium Citrate Tribasic dehydrate, 0.05% Tween 20) for 45 minutes. The endogenous peroxidase activity was eliminated by incubation with 0.3% hydrogen peroxide in a moist chamber for 30 minutes. Nonspecific binding was blocked by incubation with 2% normal goat serum in PBS containing 1% BSA (PBS-BSA), which was also used to dilute all subsequent antibodies.

At immuno-detection stage, antibodies were incubated with specimens for 2 hours at room temperature at the following final concentrations: purified mouse IgG (negative control), 1 µg/ml; biotinylated 1F11, 3.3 µg/ml; biotinylated 2F10, 7.18 µg/ml. The negative control slide was washed 5 times for 5 min each in PBS-T and then incubated with 1:1000 HRP-conjugated goat anti-mouse antibody at room temperature for 1 hour. The test sample slides were washed 5 times for 5 min each in PBS-T before signal detection with the ABC Elite kit (Vector Laboratories, Inc.: Cat. No PK-6105) and diaminobenzidine (DAB) as substrate. Conventionally stained slides (with methylene blue) were examined under light microscopy.

Cell Adhesion Assay. The optimal dosage of OPN as a cell-adhesion promoting factor was determined by following a procedure from Liaw, et al., 1994. In brief, a 96-well Maxisorp plate (Nunc, Naperville, Ill.) was coated with 100 µl/well of h-FL OPN that was 2-fold serially diluted from 500 nmol to 3.9 nmol. 1×PBS coated wells were used as negative control (0.0 nmol). The mouse embryonic fibroblasts cell line, MEF; the mouse mammary tumor cell line, PyVT and the non-invasive breast cancer cell line, MCF-7 (kindly provided by Dr. Lucy Liaw, MMCRI, Maine) were added to the plate at approximately 30,000 cells/well. After adhesion at 37° C., 5% $CO_2$ for 30-90 minutes, non-adhering cells were rinsed off with PBS and the adhering cells were fixed with 4% paraformaldehyde, stained with 0.5% toluidine blue, solubilized with 1-10% SDS and read in a microtiter plate reader at 595 nm.

After the optimal OPN dosage was determined, the inhibitive effect of the anti-OPN antibodies to cell adhesion was tested with two cell lines, MEF and PyVT. Briefly, a 96-well plate was coated with h-FL OPN at 62.5 nM and the anti-OPN antibodies were added to the wells 30 minutes before cell adhesion. A monoclonal antibody against CD62-P (IE3) was used as the negative control.

Papillary Thyroid Carcinoma Patient Plasma. Fourteen PTC plasma samples were collected from patients who have been diagnosed with papillary thyroid carcinomas (PTC) (effort of Dr. Al Driedger, London Health Science Center, London, Ontario, Canada). Group 1 consists of four samples from patients with less than 1 ng/ml blood thyroid globulin (Tg). Group 2 consists of the other 10 samples from patients waiting for $^{131}$I radiation therapy. The blood was collected in EDTA (ethylenediaminetetraacetic acid); the plasma were separated and frozen at −80° C. within 4 hours of collection.

Kidney Transplant Patient Plasma and Urine Samples. Sixty-one kidney transplant patient samples, including 26 urine samples (3 pre-transplant and 22 post-transplant samples) and 35 plasma samples (13 pre-transplant and 22 post-transplant samples) were generously provided by Dr. John Vella, Nephrology and Transplantation Center, Maine Medical Center, Portland, Me. All patients had kidney diseases and were qualified for the kidney transplant. Plasma was also collected from 21 healthy volunteer blood donors who formed the control group.

Sandwich (Two-Antibody) ELISA for OPN Measurement. A two-antibody Sandwich ELISA was developed as a quantitative ELISA for OPN measurement. MAb 2F10, which binds specifically to the N-terminal of OPN, was selected as the capture antibody; while 1F11, specific for the C-terminal, was selected as the determination antibody (1F11 was biotinylated). This assay design aimed to identify only relatively intact OPN molecules that were in a sample.

Initially, chessboard titration experiments (Crouther, et al., volume 149; setting up the assay in a "chessboard" pattern takes into account the variability inherent to the assay plate and the detection system) were carried out to determine the optimal concentrations of capture antibody 2F10 and detection antibody 1F11. It was determined that 2F10 at 1.5 µg/ml and 1F11 at 0.6 µg/ml would be the optimal antibody concentrations for the sandwich ELISA.

This assay was then performed by first establishing an OPN-dosage response curve (standard curve), which was used to determine the OPN quantity in a sample. All samples were run in triplicates and undiluted. The capture antibody, 2F10, was diluted 1:500 (1.5 µg/ml) in PBS and added to a 96-well flat bottom ELISA plates (BD Falcon, VWR) at 100 µl/well. After coating at 4° C. overnight, the plate was rinsed twice with PBS-T before being blocked with 3% nonfat milk in PBS-T at 37° C. for 1 hour.

Subsequently, 100 µl of serially diluted OPN standards or 50 µl of patient plasma or urine samples were added to each well followed by 1-hour incubation at 37° C. The standards were comprised of 100 µl/well of h-FL OPN 2-fold serially diluted from 5.0 to 0.002 µg/ml. After 4× washing with PBS-T, the detection antibody, biotinylated 1F11 diluted 1:500 (0.6 µg/ml) in 3% nonfat milk in PBS-T, was added and the plate was incubated at 37° C. for 2 hours. Following the second washing, 1:500 (2 µg/ml) diluted HRP-conjugated streptavidin was added and the plate incubated at 37° C. for 1 hour. After the final wash, TMB substrate was added to develop color.

Results

Antibody Titration for Serum from Immunized Mouse. The serum obtained from mouse strain 1284 on Day 170 after five immunizations was subjected to ELISA testing to determine the activity of the anti-OPN antibodies. The titer was $3.125 \times 10^3$, indicating that the mouse had produced sufficient anti-OPN antibodies and it was ready for using in fusion experiment (FIG. 1).

Hybridoma Screening. In order to identify those hybridoma cultures producing anti-OPN antibodies, an initial ELISA screening of the hybridoma supernatants was performed after 14 days of fusion. Six hybridoma cultures were identified secreting antibodies (IgG or IgM) against human full-length (h-FL) OPN, and four of them (1284:4E8, 1284:2B11, 1284:3G11 and 1284:2C10) produced high antibody activities. The other two hybridomas (1284:4F8 and 1284:1H4) initially produced antibodies at lower activities; nevertheless, these two hybridomas were able to achieve satisfactory antibody levels after further screening procedures (see, Materials and Methods): from "+" to "+++" for 1284:4F8 and from "+" to "++" for 1284:1H4 (Table 2).

In order to verify which types of antibodies they were producing, these six hybridoma cultures were expanded and the second ELISA screening was performed with three control antigens including GSTOPN (cleaved human full-length OPN), control His-tagged swine viral protein, and 1×PBS, along with HRP-conjugated goat anti-mouse IgG (Fc$_\gamma$ specific) as the secondary antibody. The results showed that all six primary hybridomas secreted IgG against OPN.

Subcloning. Five randomly selected hybridoma cultures (1283:1C12, 1283:2G8, 1284:4E8, 1284:2B11 and 1284:3G11) were subcloned immediately by limiting dilution to generate monoclones. Two of them, 1283:1C12 and 1283:2G8, were produced previously in our lab. These two hybridomas were prepared from frozen stocks. After 1-3 times of repetitive subcloning, 25 monoclones were obtained from the five primary hybridoma cultures (Table 3), five of which (2F9, 2C5, 2H9, 1F11 and 2F10) were appeared promising and subjected to further characterization.

Development hierarchy of the anti-OPN monoclonal antibodies (Table 3). The single cell subcloning technique was applied to 1283:1C12, 1283:2G8, 1284:4E8, 1284:2B11, and 1284:3G11 primary hybridoma cultures, obtained after the fusion experiments, which showed strong antibody activities in ELISA. Circled names indicate monoclones. Bold italic fonts indicate the five monoclones selected for further studies.

For example, in the first subcloning procedure for cell culture 1283:1C12, cells from well 2F5 were subjected for the second subcloning. Subsequently, cells from well 1D1 were chosen for the third round, resulting in monoclones 1C9, 2B3, 2E11, and 2F9. Finally, 2F9 was selected for further studies and the other three clones were cryo preserved in liquid nitrogen.

TABLE 3

Development Hierarchy of the Hybridomas Producing Anti-OPN Monoclonal Antibodies

| Primary hybridoma cell culture | 1283: 1C12 | 1283: 2G8(N) | 1284: 4E8(N) | 1284: 2B11(C) | 1284: 3G11(N) |
|---|---|---|---|---|---|
| 1st Subcloning | 2F5 | 1B12 | 1A7 1B7 1B10 2B7 2F10 2F3 | 1D4 *1F11* | 1B9 1D11 1E8 1G12 2A1 2A2 2B9 2C6 *2F10* |
| 2nd Subcloning | 1D1 | 1G2 1G10 *2C5* | 1B6 1E10 1E12 1F3 2A5 2C9 *2H9* | | |
| 3rd Subcloning | 1C9 2B3 2E11 *2F9* | | | | |

Production of Ascite Fluid. Because the FO myeloma cells (e.g., ATCC, Bethesda, Md.: Cat. No. CRL 1646) were derived from a Balb/cJ mouse and splenocytes were from OPN—null mice of C57BL origin ($H-2^b$), a heterozygous mouse strain ($H-2^{b/d}$) crossed from the C57BL and the Balb/cJ mice, as well as an unrelated athymic nude strain, were used for ascite fluid production.

Information regarding each mouse used for ascite fluid collection, as well as the total volumes of acsite fluid collected for each monoclonal antibody is listed in Table 4. The total volumes of ascite fluid collected from each MAb were 2E11: 28.8 ml; 2C5: 26.7 ml; 2H9: 30.3 ml; 1F11: 31.5 ml; and 2F10: 43.0 ml.

TABLE 4

Collection of Ascite Fluids

| Mouse Strain | DOB | Sex | Parents | Mouse ID | MAbs | Ascite Volume (ml) | Sum (ml) |
|---|---|---|---|---|---|---|---|
| Balbc/JxOPN-/- C57B46 | Jan. 23, 2006 | female | Balbc/Jx1940 | 2250 | 1F11 | 3 | 31.5 |
| Balbc/JxOPN-/- C57B46 | Jan. 23, 2006 | female | Balbc/Jx1940 | 2251 | 1F11 | 4.5 | |
| Balbc/JxOPN-/- C57B46 | Jan. 23, 2006 | male | Balbc/Jx1940 | 2252 | 1F11 | 3 | |
| Balbc/JxOPN-/- C57B46 | Jan. 23, 2006 | male | Balbc/Jx1940 | 2253 | 1F11 | 1.5 | |
| Balbc/JxOPN-/- C57B46 | Jan. 23, 2006 | male | Balbc/Jx1940 | 2254 | 1F11 | 4.5 | |
| Balbc/JxOPN-/- C57B46 | Mar. 13, 2006 | female | Balbc/Jx1948 | 2352 | 1F11 | 4.5 | |
| Balbc/JxOPN-/- C57B46 | Mar. 13, 2006 | female | Balbc/Jx1948 | 2353 | 1F11 | 6 | |
| Hsd-Athymicnude-Foxninu | Feb. 7, 2005 | male | Harlan | 34 | 1F11 | 4.5 | |
| Balbc/JxOPN-/- C57B46 | Dec. 28, 2005 | female | Balbc/Jx1781 | 2235 | 2C5 | 7 | 26.7 |
| Balbc/JxOPN-/- C57B46 | Dec. 28, 2005 | female | Balbc/Jx1781 | 2236 | 2C5 | 3 | |
| Balbc/JxOPN-/- C57B46 | Dec. 28, 2005 | female | Balbc/Jx1781 | 2237 | 2C5 | 2.5 | |
| Balbc/JxOPN-/- C57B46 | Dec. 28, 2005 | female | Balbc/Jx1781 | 2238 | 2C5 | 2.7 | |
| Balbc/JxOPN-/- C57B46 | Dec. 30, 2005 | male | Balbc/Jx1948 | 2241 | 2C5 | 1.5 | |
| Balbc/JxOPN-/- C57B46 | Dec. 30, 2005 | male | Balbc/Jx1948 | 2242 | 2C5 | 2 | |
| Balbc/JxOPN-/- C57B46 | Dec. 30, 2005 | male | Balbc/Jx1948 | 2243 | 2C5 | 1.5 | |
| Hsd-Athymicnude-Foxninu | Feb. 7, 2005 | male | Harlan | 32 | 2C5 | 6.5 | |
| Balbc/JxOPN-/- C57B46 | Dec. 28, 2005 | male | Balbc/Jx1781 | 2233 | 2E11 | 7.5 | 28.8 |
| Balbc/JxOPN-/- C57B46 | Dec. 28, 2005 | male | Balbc/Jx1781 | 2234 | 2E11 | 8 | |
| Balbc/JxOPN-/- C57B46 | Dec. 30, 2005 | male | Balbc/Jx1948 | 2240 | 2E11 | euthanized | |
| Balbc/JxOPN-/- C57B46 | Mar. 13, 2006 | male | Balbc/Jx1948 | 2347 | 2E11 | 2 | |
| Balbc/JxOPN-/- C57B46 | Mar. 13, 2006 | male | Balbc/Jx1948 | 2348 | 2E11 | 4 | |
| Hsd-Athymicnude-Foxninu | Feb. 7, 2005 | male | Harlan | 31 | 2E11 | 2.8 | |
| Hsd-Athymicnude-Foxninu | Feb. 7, 2005 | male | Harlan | 35 | 2E11 | 4.5 | |
| Balbc/JxOPN-/- C57B46 | Jan. 23, 2006 | male | Balbc/Jx1948 | 2255 | 2F10 | 5 | 43 |
| Balbc/JxOPN-/- C57B46 | Jan. 23, 2006 | male | Balbc/Jx1948 | 2256 | 2F10 | 5.5 | |
| Balbc/JxOPN-/- C57B46 | Jan. 23, 2006 | male | Balbc/Jx1948 | 2257 | 2F10 | euthanized | |
| Balbc/JxOPN-/- C57B46 | Mar. 13, 2006 | female | Balbc/Jx1948 | 2343 | 2F10 | 4 | |
| Balbc/JxOPN-/- C57B46 | Mar. 13, 2006 | female | Balbc/Jx1948 | 2344 | 2F10 | 4 | |
| Balbc/JxOPN-/- C57B46 | Mar. 13, 2006 | female | Balbc/Jx1948 | 2345 | 2F10 | 1.5 | |

TABLE 4-continued

Collection of Ascite Fluids

| Mouse Strain | DOB | Sex | Parents | Mouse ID | MAbs | Ascite Volume (ml) | Sum (ml) |
|---|---|---|---|---|---|---|---|
| Balbc/JxOPN−/− C57B46 | Mar. 13, 2006 | male | Balbc/Jx1948 | 2346 | 2F10 | 5 | |
| Balbc/JxOPN−/− C57B46 | Mar. 13, 2006 | female | Balbc/Jx1948 | 2349 | 2F10 | 4 | |
| Balbc/JxOPN−/− C57B46 | Mar. 13, 2006 | female | Balbc/Jx1948 | 2350 | 2F10 | 4.5 | |
| Balbc/JxOPN−/− C57B46 | Mar. 13, 2006 | female | Balbc/Jx1948 | 2351 | 2F10 | 5.5 | |
| Hsd-Athymicnude-Foxninu | Feb. 7, 2005 | male | Harlan | 36 | 2F10 | 4 | |
| Balbc/JxOPN−/− C57B46 | Dec. 28, 2005 | female | Balbc/Jx1781 | 2239 | 2H9 | euthanized | 30.3 |
| Balbc/JxOPN−/− C57B46 | Dec. 30, 2005 | male | Balbc/Jx1948 | 2244 | 2H9 | 2.5 | |
| Balbc/JxOPN−/− C57B46 | Dec. 30, 2005 | male | Balbc/Jx1948 | 2245 | 2H9 | 2.5 | |
| Balbc/JxOPN−/− C57B46 | Dec. 30, 2005 | female | Balbc/Jx1948 | 2246 | 2H9 | 4.5 | |
| Balbc/JxOPN−/− C57B46 | Dec. 30, 2005 | female | Balbc/Jx1948 | 2247 | 2H9 | 4.5 | |
| Balbc/JxOPN−/− C57B46 | Dec. 30, 2005 | male | Balbc/Jx1948 | 2248 | 2H9 | 1.5 | |
| Balbc/JxOPN−/− C57B46 | Dec. 30, 2005 | female | Balbc/Jx1948 | 2249 | 2H9 | 5 | |
| Hsd-Athymicnude-Foxninu | Feb. 7, 2005 | male | Harlan | 33 | 2H9 | 9.8 | |
| Total Ascite volume (ml) | | | | | | | 160.3 |

Verification of MAbs Purity. The total volumes of the purified and biotinylated MAbs and their antibody concentrations were listed in Table 5. Antibodies 2E11, 2C5 and 2H9 were purified from 1 ml of each antibody ascite fluid. Antibodies 1F11 and 2F10 were purified from 2 ml ascite fluid. The final concentration of each antibody was 0.23 mg/ml, 1.4 mg/ml, 0.40 mg/ml, 0.9 mg/ml and 0.75 mg/ml, respectively, with the total volume of 3 ml, 2.5 ml, 3.5 ml, 6.5 ml and 4.6 ml in 1×PBS, respectively. Only the 1F11 and 2F10 antibodies were subject to biotin-labeling from 1 ml of each purified antibody. The final concentration of these biotinylated antibodies was 0.33 mg/ml and 0.718 mg/ml with the volume of 1 ml and 0.8 ml, respectively.

TABLE 5

Information of Purified MAbs

| Purified MAbs | Concentration (mg/ml) | Volume (ml) |
|---|---|---|
| 2E11 | 0.23 | 3 |
| 2C5 | 1.4 | 2.5 |
| 2H9 | 0.40 | 3.5 |
| 1F11 | 0.9 | 5.5 |
| 2F10 | 0.75 | 3.6 |
| Biotinylated-1F11 | 0.33 | 1 |
| Biotinylate-2F10 | 0.718 | 0.8 |

Figure 2A:
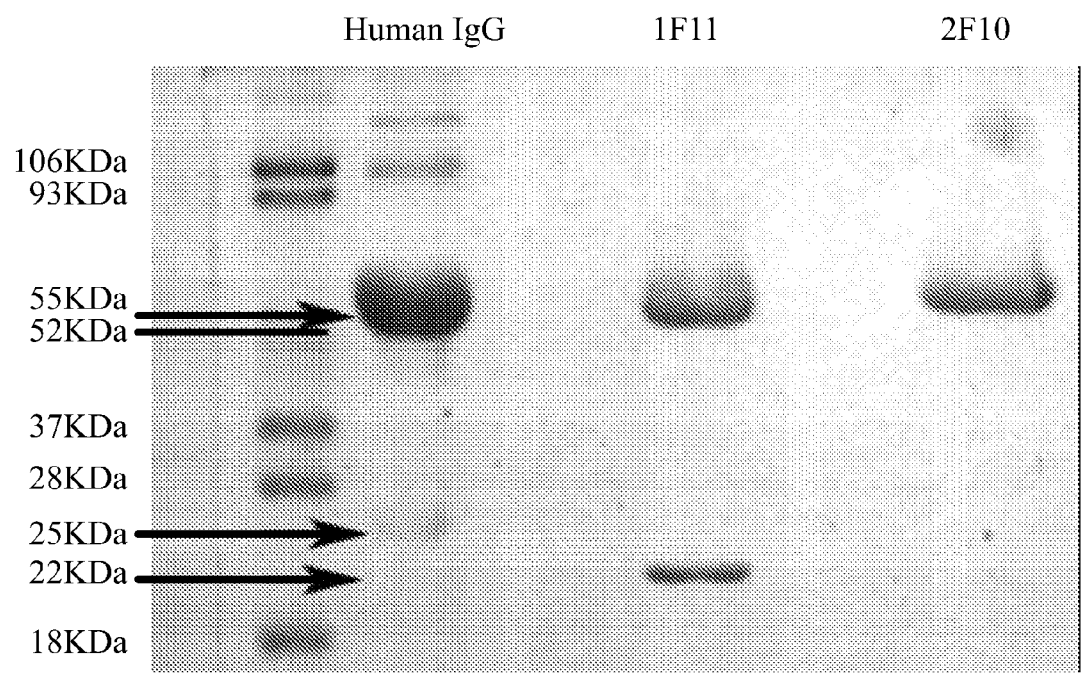
FIG. 2 shows an SDS-PAGE analysis of purified MAbs against OPN using antibodies 1F11 and 2F10 (2A) and 2E11, 2C5 and 2H9 (2B).
Figure 2B:
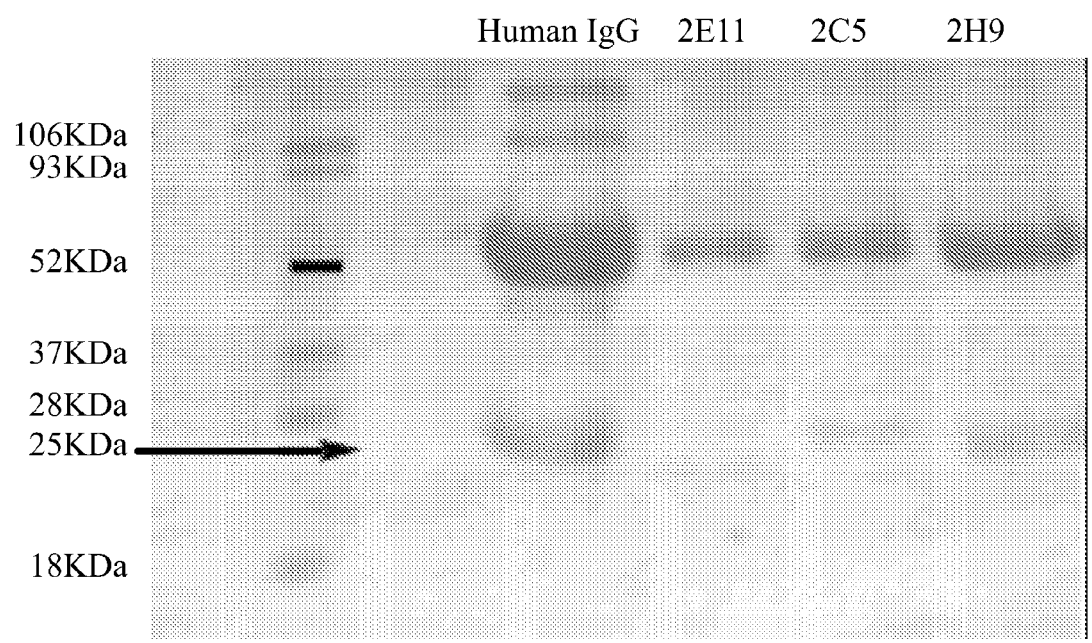

In order to determine the purities of the five MAbs—2E11, 2C5, 2H9, 1F11, and 2F10—the samples were resolved with SDS-PAGE and stained with Coomassie blue. In brief, the anti-OPN MAbs were purified from ascites fluids using a Protein G column. The samples were loaded onto a 12.5% SDS—polyacrylamide gel under reducing condition. After Coomassie blue staining the two bands representing the heavy chain (~55 KDa) and the light chain (~25 KDa) of IgG are clearly visible. A purified human IgG sample served as a positive control. MAb 1F11 shows a 55 KDa and a 25 KDa bands (FIG. 2A) and MAb 2F10 shows a 55 KDa band (FIG. 2B). Each of the MAbs 2E11, 2C5, and 2H9 shows a 55 KDa and a 25 KDa band. The molecular weight protein standards (Bio-Rad) are shown as indicated. All MAbs except 2F10 showed a 55 kDa and a 25 kDa band, representing the heavy chain (~55 kDa) and the light chain (~25 kDa) of IgG, respectively (FIGS. 2A, B). Antibody 2F10 only displayed a band at 55 kDa (FIG. 2A).

Figure 3A:
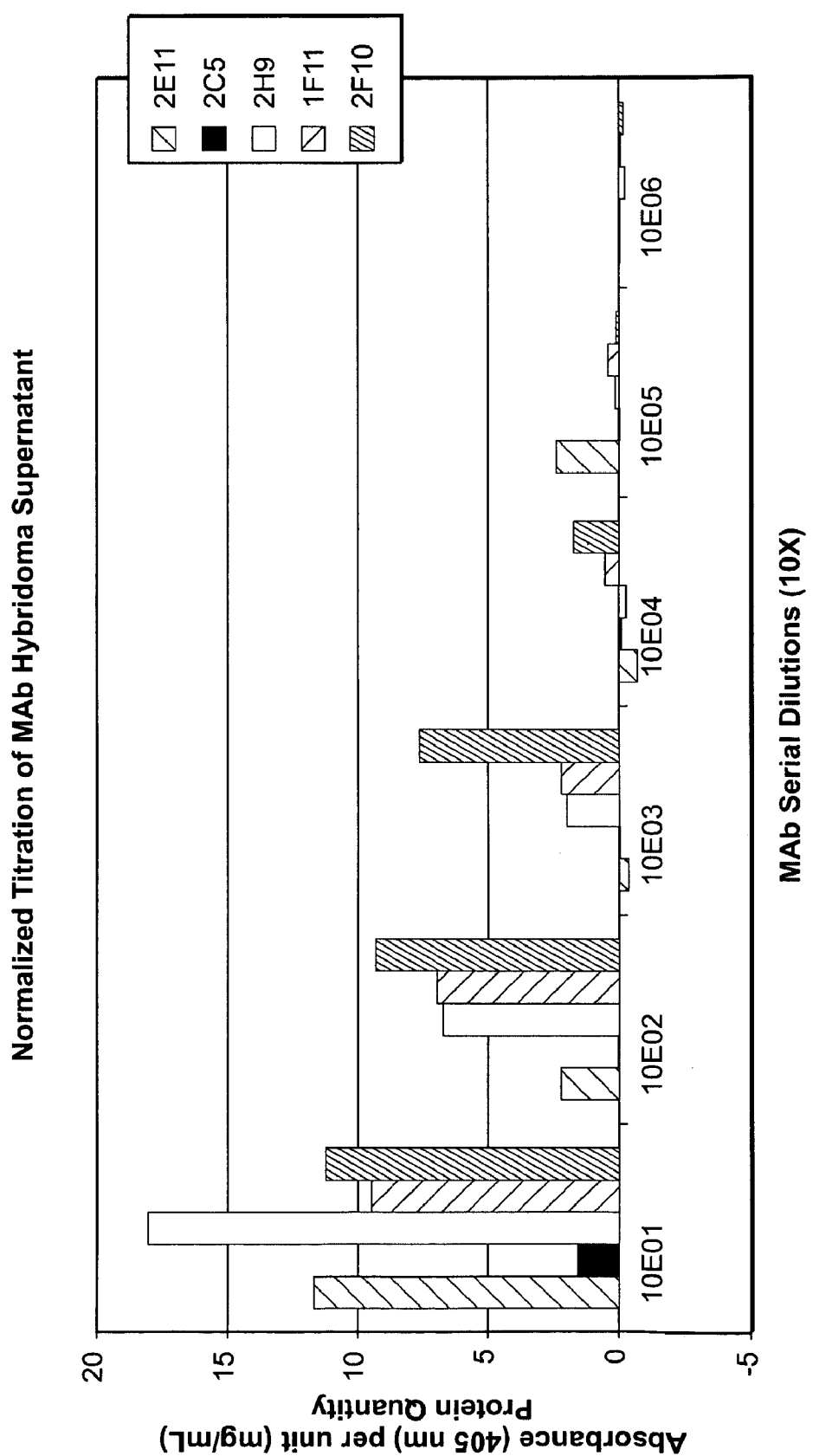
FIG. 3 shows normalized titration of (3A) hybridoma supernatant, (3B) ascite fluid and (3C) biotinylated MAbs. The assays were preformed using an ELISA assay with 10-fold serially diluted antibodies. The antibody titers were normalized based on their concentrations using the following formula: Titer=A405 nm/Starting Antibody Concentration (mg/ml).

Normalized Titration of Hybridoma Culture Supernatants, Purified MAbs, and Biotinylated MAbs. Large amounts of MAb supernatant and ascite fluid were collected. The supernatant was collected by growing hybridoma cell lines in a 175-cm² tissue culture flask until the culture media turned yellow. The ascite fluid was collected by injecting hybridoma cells into the mouse and purified using protein G column. In order to determine the activities of different antibodies, titration testing was performed using ELISA with 10-fold serially diluted antibodies. The resulting titers were normalized based on their concentrations so that comparable amounts of antibodies could be used for subsequent experiments. FIGS. 3A and B showed that the ascite fluid had much higher antibody activities than the supernant had. For example, the titer for 2E11 in 100× diluted ascite fluid was ~59 absorbance units per mg/ml antibody while in 10× diluted supernatant, it was ~12 absorbance units per mg/ml antibody, which translated into a ~50× higher antibody activity in the ascite fluid. This observation was consistent with the known fact that ascite fluid in general produces higher antibody concentrations than supernatant. However, the 2C5 activity was low in both the supernatant and the ascite fluid (the titer was ~3 absorbance units per mg/ml antibody in 100× diluted ascite fluid). The reason leading to the low 2C5 activity was not clear.

Figure 3B:
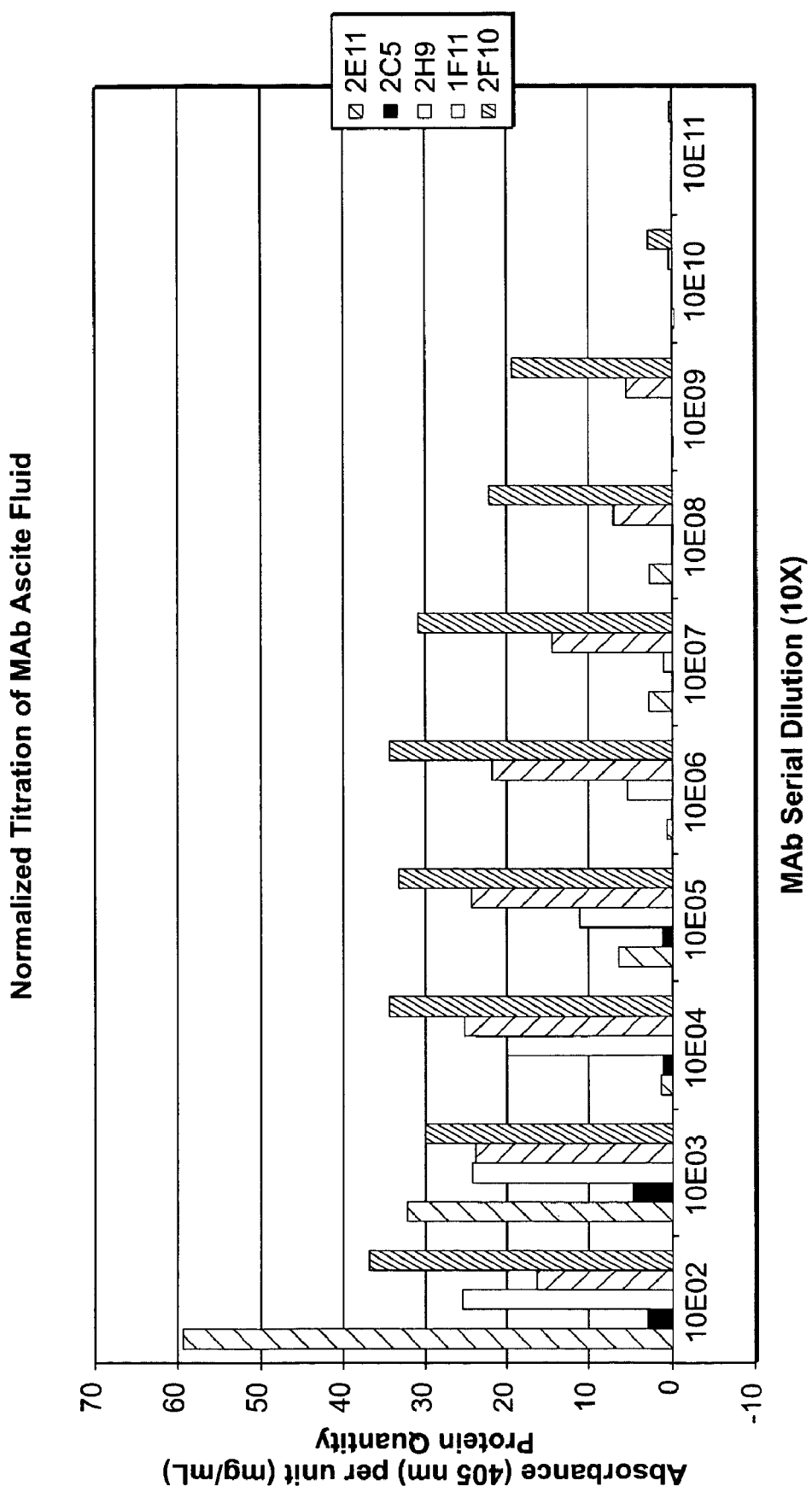
Figure 3C:
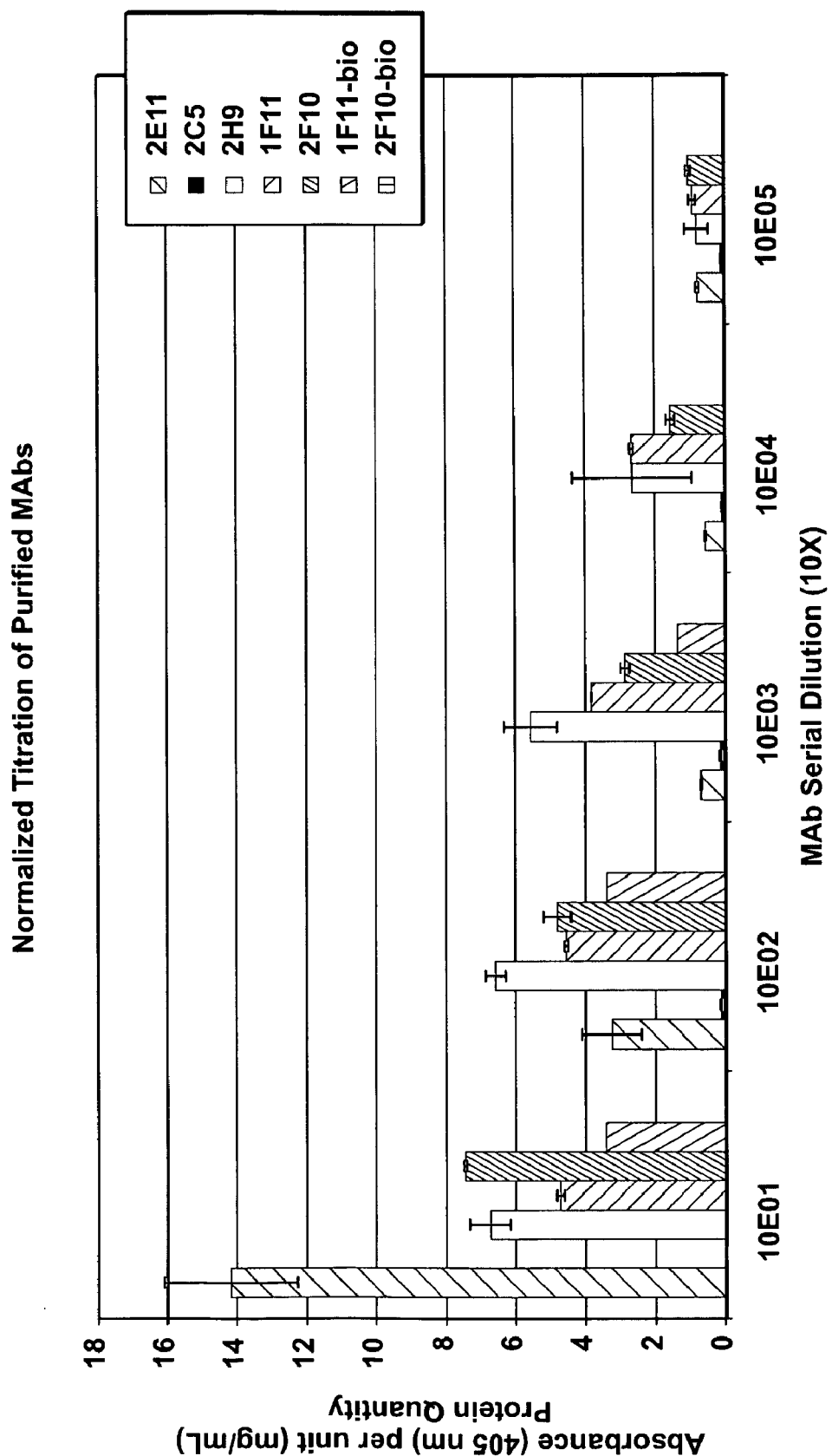

After being purified from the ascite fluid, the majority of the antibodies activities were lost, probably because of protein denaturation during elution (FIGS. 3 A-C). For example, purified 2E11 titer was ~14 absorbance units per mg/ml antibody in 10× diluted buffer compared to ~59 absorbance units per mg/ml antibody in 100× diluted ascite fluid. Column leaching was unlikely because little or no proteins were detected in the column flow-through. 2C5 lost all of its activity after purification. Similarly, 1F11 still retained most of its activity while 2F10 lost almost all the antibody activity after biotinylation (FIG. 3C). This observation was consistent with a previous report that a loss of antibody immunoreactivity of some of the leukocyte surface proteins occurred after using NHS-Biotin to label cells (Yates, et al., 1988).

Isotyping of MAbs 2E11, 2C5, 2H9, 1F11 and 2F10. The immunoglobulin isotype of each MAb was determined using IsoStrip Mouse Monoclonal Antibody Isotyping strip. The isotype of the MAbs 2F9, 2C5, 2H9, 1F11 and 2F10 was IgG1 subtype, with a κ light chain. Hybridoma supernatants were used in all ELISA and Western blot assays described in this section unless noted otherwise.

Figure 4:
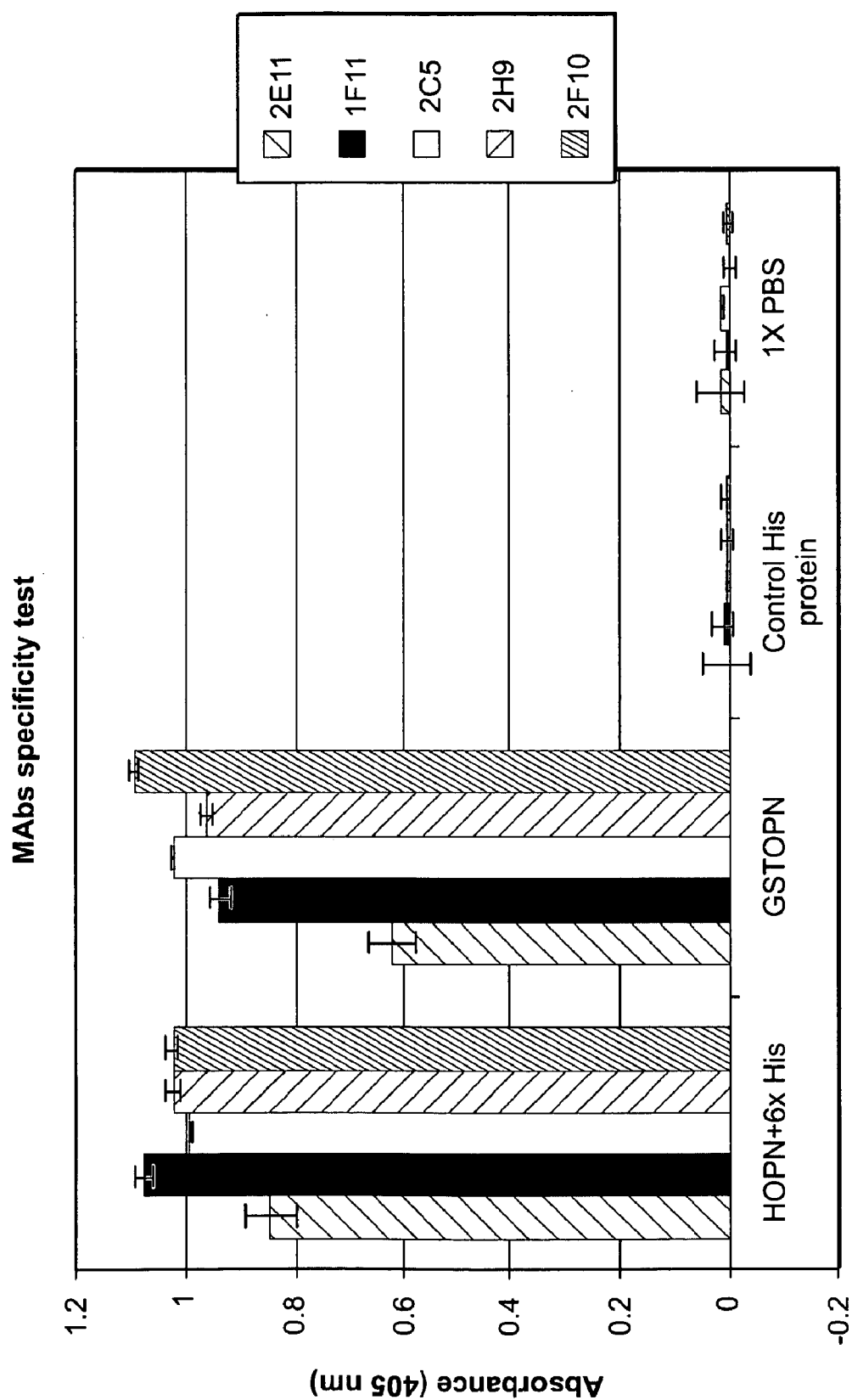
FIG. 4 shows specificity differentiation testing of the anti-OPN monoclonal antibodies using an ELISA. Error bar+1 standard error of mean (SEM).

Differential ELISA of MAbs. In an attempt to confirm that the MAbs reacts specifically with the OPN protein but not with the His-tag, GSTOPN (GST cleaved), a recombinant human OPN without His-tag, was used in addition to h-FL OPN as the test antigens in the ELISA testing. Antibodies 2E11, 1F11, 2C5, 2H9 and 2F10 were tested against h-FL OPN with 6×His-tag, GSTOPN (recombinant OPN with GST tag cleaved), control swine viral protein with 21×His-tag, and PBS with 3% none fat dry milk. The figure showed that these five antibodies tested positive against h-FL His OPN and h-FL OPN with GST cleaved but negative against either the control His-tagged protein or PBS with 3% none fat dry milk (negative control). A control His protein, a recombinant swine viral protein with 21×His-tag but no OPN sequence, was used alongside as the negative antigen. FIG. 4 shows that all the MAbs reacted with h-FL OPN and GSTOPN but not with the control His protein confirming that these antibodies were specifically reactive against OPN.

Figure 5A:
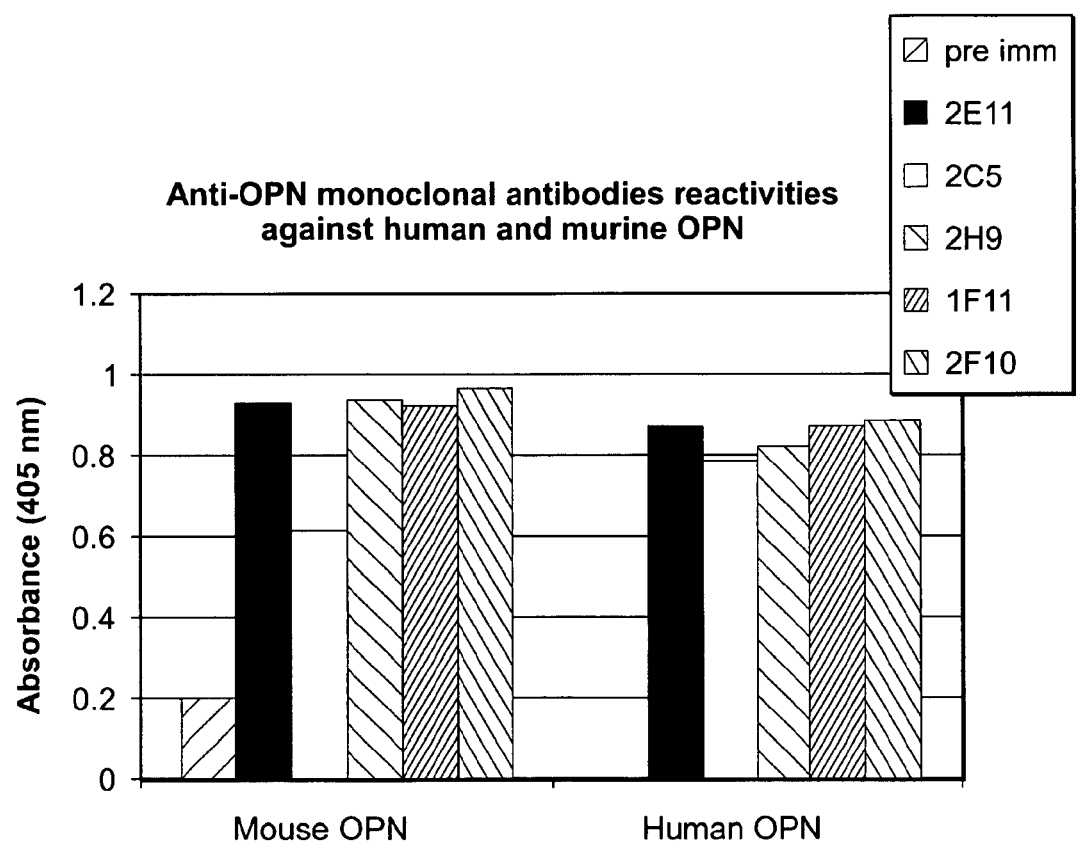
FIG. 5 shows cross-reactivity of MAbs against human and mouse OPN. The supernatants from the five monoclonal hybridoma (2E11, 2C5 2H9, 1F11 and 2F10) were probed against h-FL OPN and m-FL OPN in (5A) ELISA and in Western blot (5B=human probe and 5C=murine probe).
Figure 5B:
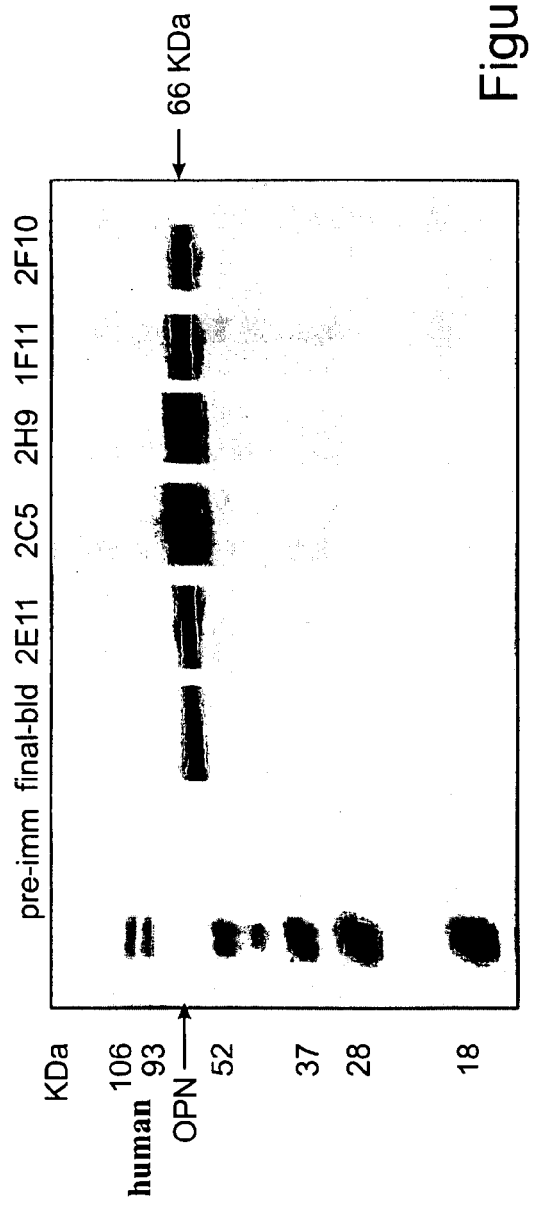
Figure 5C:
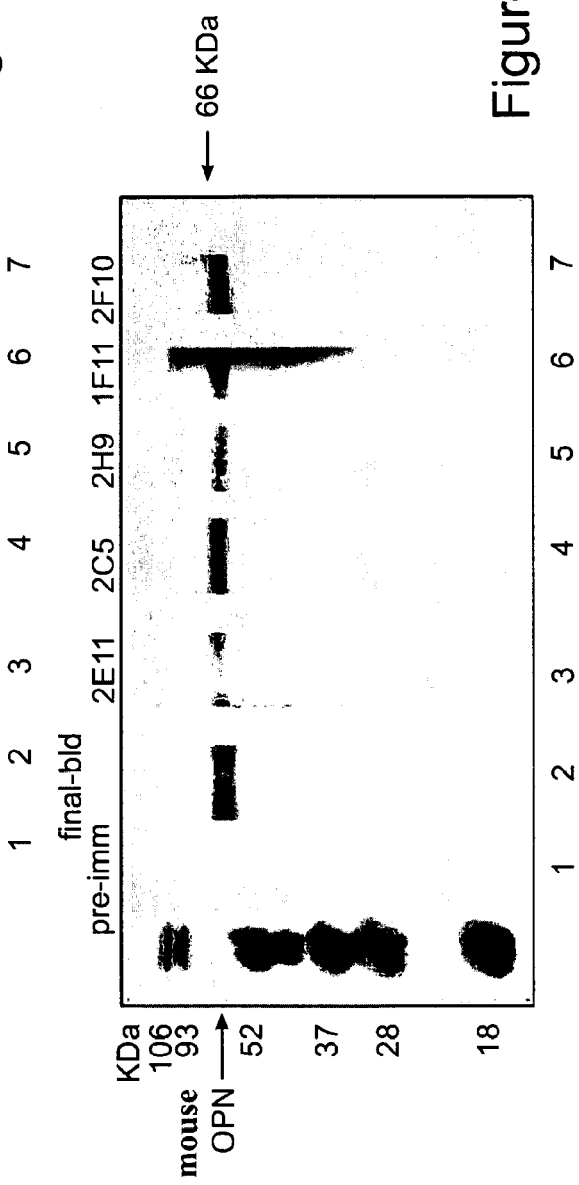

Cross-species OPN reactivities of MAbs. Although the MAbs were made against recombinant human OPN they might also react with other mammalian OPNs since they were products of B cells from OPN. In order to elucidate this, the supernatants from these five monoclonal hybridomas were probed against h-FL OPN and m-FL OPN in an ELISA (FIG. 5A) and in Western blot (FIGS. 5B & 5C). In the ELISA, the wells were coated with h-FL OPN and m-FL OPN, respectively. The results showed that all five antibodies 2E11, 2C5, 2H9, 1F11, and 2F10 recognized OPN from both species. In the Western blot 20 ng of His-tagged h-FL OPN were loaded in each lane of 12.5% polyacrylamide gel. After the electrophoresis the proteins were blotted onto a PVDF membrane and each lane was cut into a strip to be probed with each antibody. The result showed that all five MAbs 2E11, 2C5, 2H9, 1F11 and 2F10 identified a 66-KDa band. FIG. 5C is a repetition of the Western blot in FIG. 5B with His-tagged m-FL OPN. Similarly, all five antibodies (2E11, 2C5, 2H9, 1F11 and 2F10) identified a 66-KDa band.

The results demonstrated that these antibodies reacted with both human and mouse full-length OPNs. In ELISA, all five antibodies demonstrated significantly higher responses to mouse OPN than the pre-immune sample did. In addition, their responses to both human and mouse OPNs were comparable. This result was further corroborated by the Western blot where all five antibodies recognized the 66 kDa mouse and human OPN bands. In contrast, the pre-immune sample did not have any positive signal (FIGS. 5A, B, C).

Figure 6A:
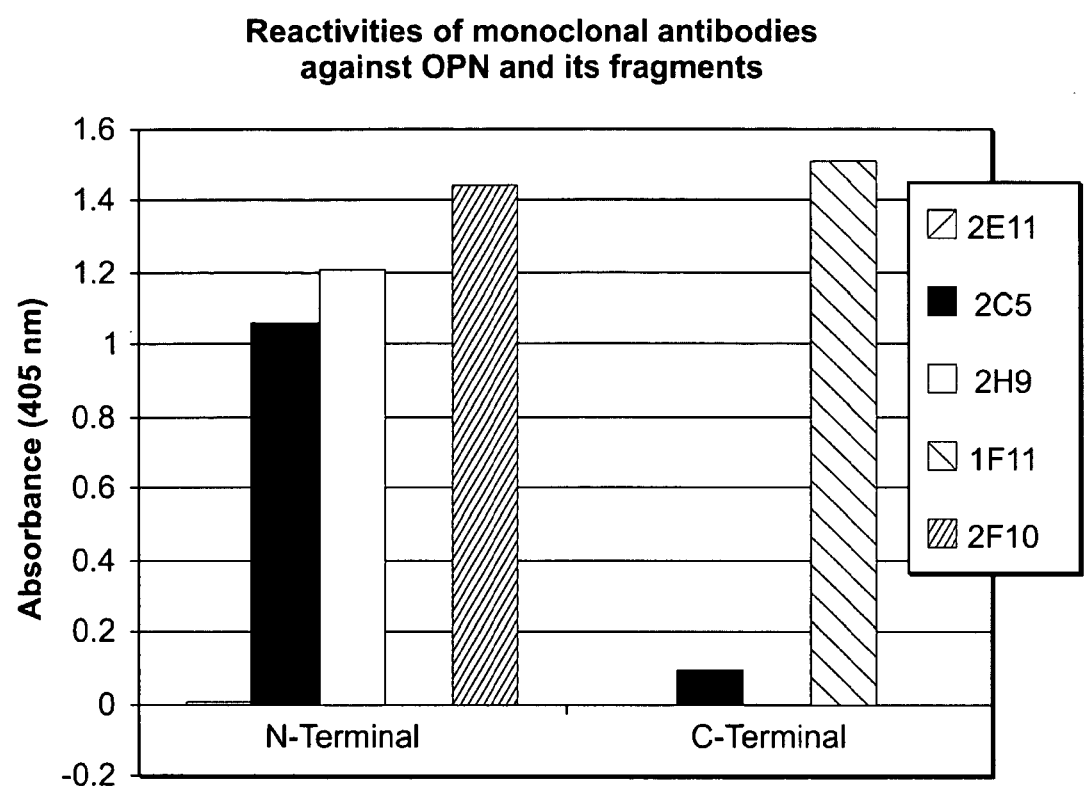
FIG. 6 shows the determination of epitope specifics on the anti-OPN MAbs by (6A) ELISA and (6B & 6C) Western blot. Antibodies were probed against N-terminal and C-terminal fragments of OPN.
Figure 6B:
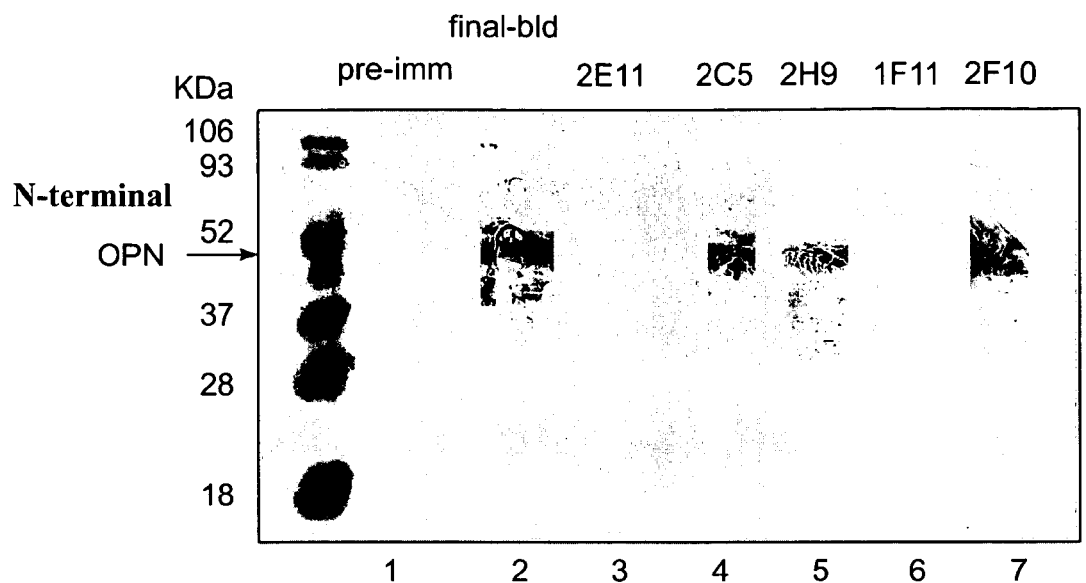
Figure 6C:
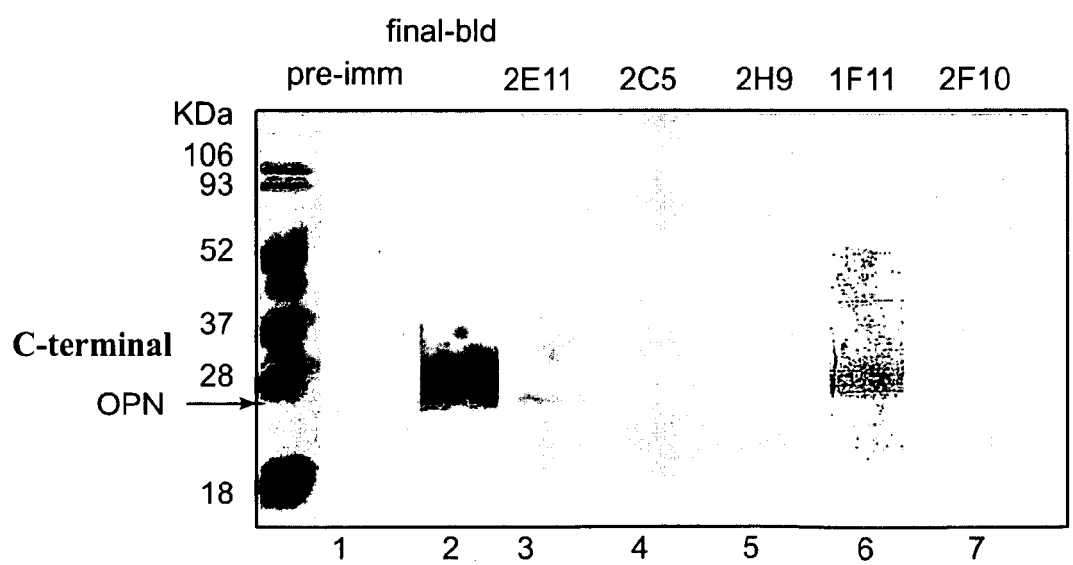

Antibodies against OPN Fragments. It was shown above that these five monoclonal antibodies recognized full-length OPN (65 KDa) (FIGS. 6A, B). In order to further identify their reactivity to the OPN epitopes two OPN fragments, N-terminal OPN (40 KDa) and C-terminal OPN (25 KDa), were tested against these five monoclonal antibodies in ELISA and in Western blot. Assays were performed as above. The ELISA test showed that MAbs 2C5, 2H9 and 2F10 recognized the N-terminal OPN (FIGS. 6A, B), 1F11 recognized the C-terminal OPN (FIGS. 6A, C), while 2E11 recognized C-OPN more strongly than 2E11. The ELISA results were further confirmed by Western blot against N-terminal OPN and C-terminal OPN.

Figure 7A:
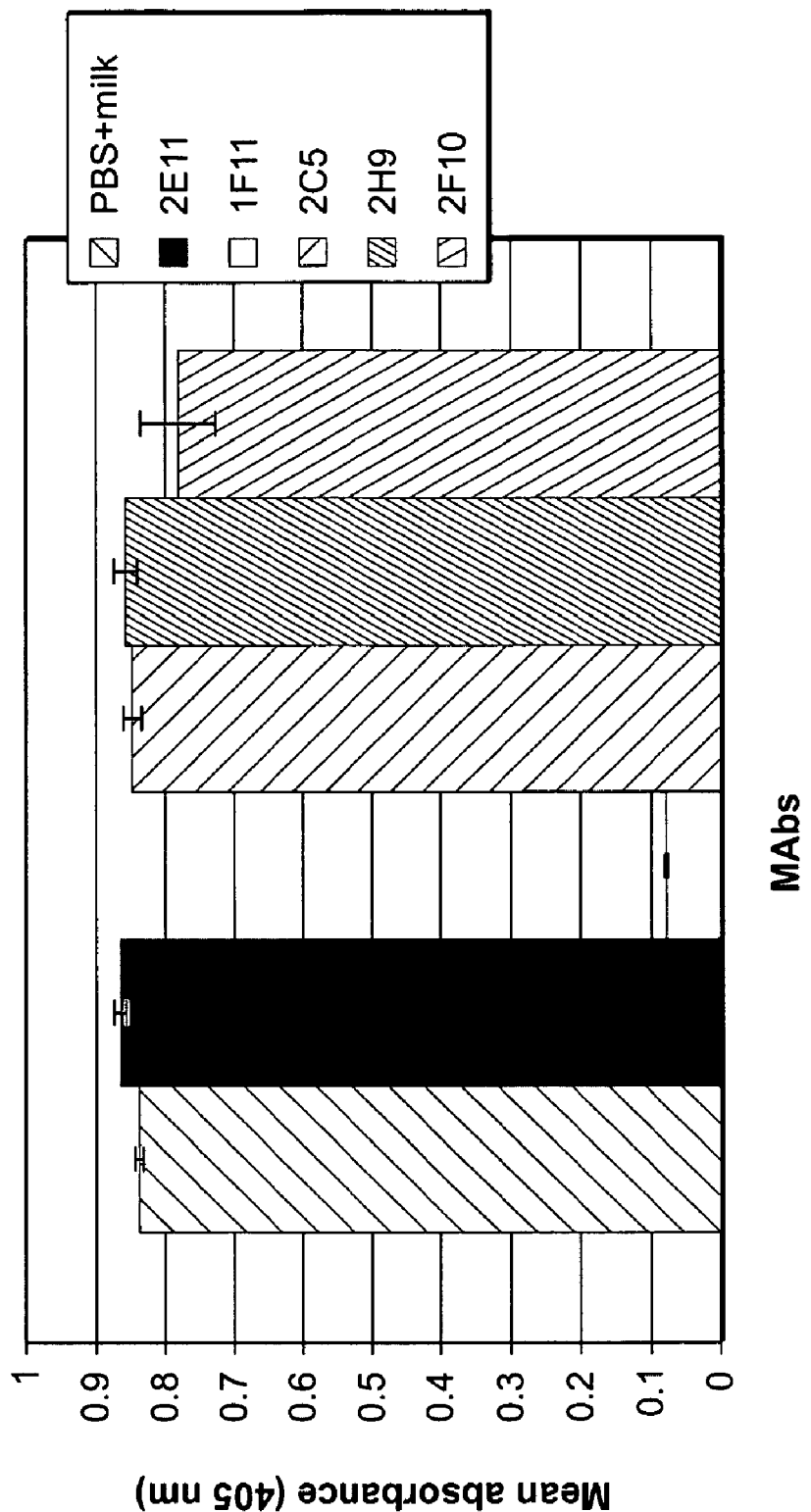
FIG. 7 shows a comparison of epitopes recognized by the MAbs of the present invention using competition ELISA against (7A) C-terminal human FL OPN and (7B) N terminal human OPN.
Figure 7B:
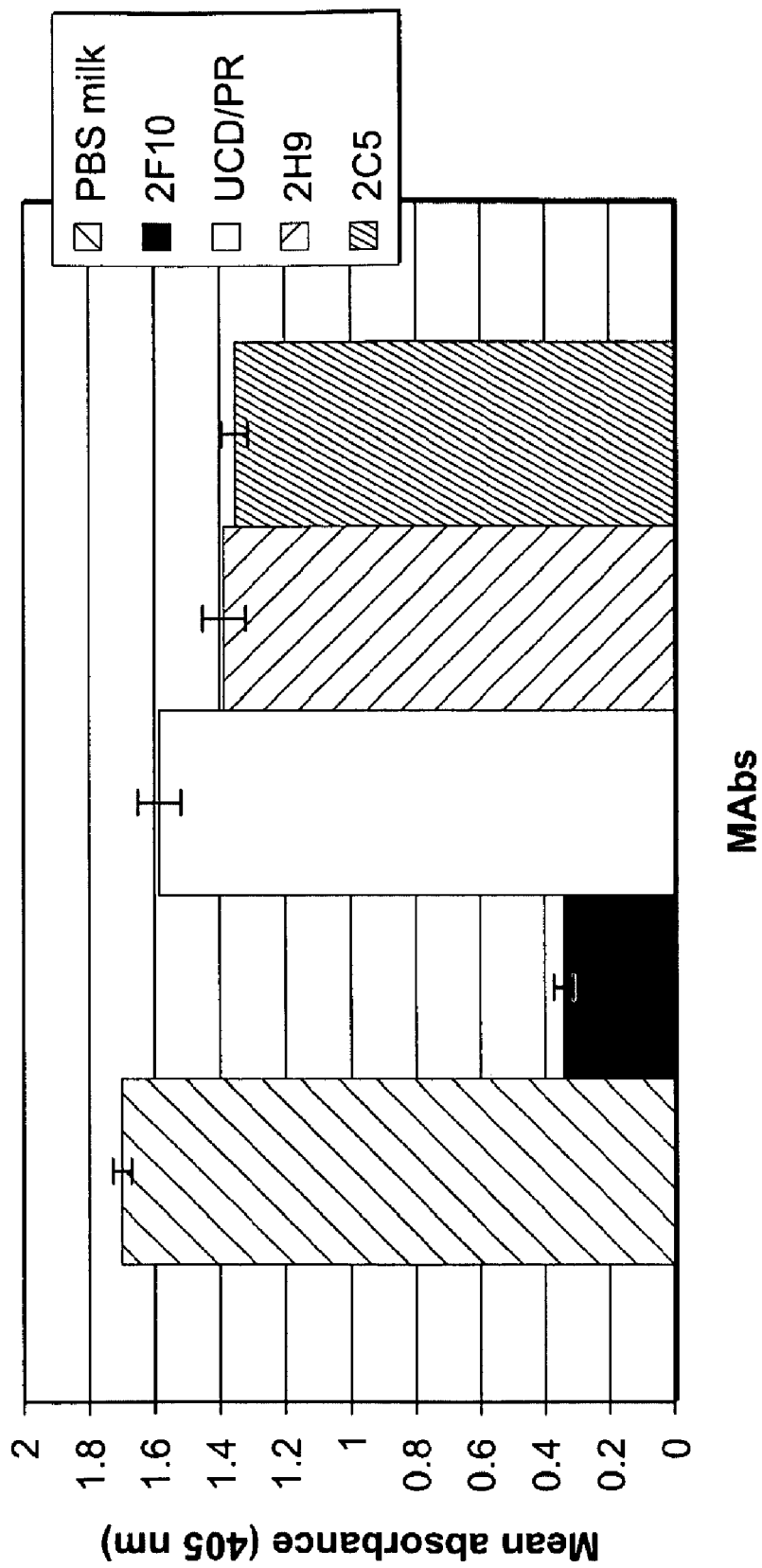

Further Antibody Epitope Mapping and Comparison. In an order to determine whether these five MAbs bind to the same epitopes on OPN, the biotinylated MAbs 1F11 and 2F10 were used to compete with the five unlabeled MAbs for binding to specific OPN epitopes using a competition ELISA assay. Epitope mapping involves a more molecular approach, e.g., phage display assay or using synthetic peptide. In this assay, the biotinylated MAbs compete with unlabeled MAbs for binding to specific OPN epitopes. Each microtiter plate well was coated with 20 ng/100 ul human FL OPN. In FIG. 7A, each well was incubated with PBS+milk (control) or one of the five unlabeled MAbs followed by addition of 1F11 biotinylated antibody. In FIG. 7B, biotinylated 2F10 was used in place of 1F11-biotinylated antibody. Biotinylated Ab binding was detected by incubation with HRP-conjugated streptavidin, followed by TMB substrate. Both FIGS. 7A and 7B showed that the biotinylated antibodies were only inhibited by their unlabeled counterparts, resulting in decreased absorbance readings. This showed that 1F11 and 2F10 recognize OPN epitopes different from those of the other MAbs.

Figure 8:
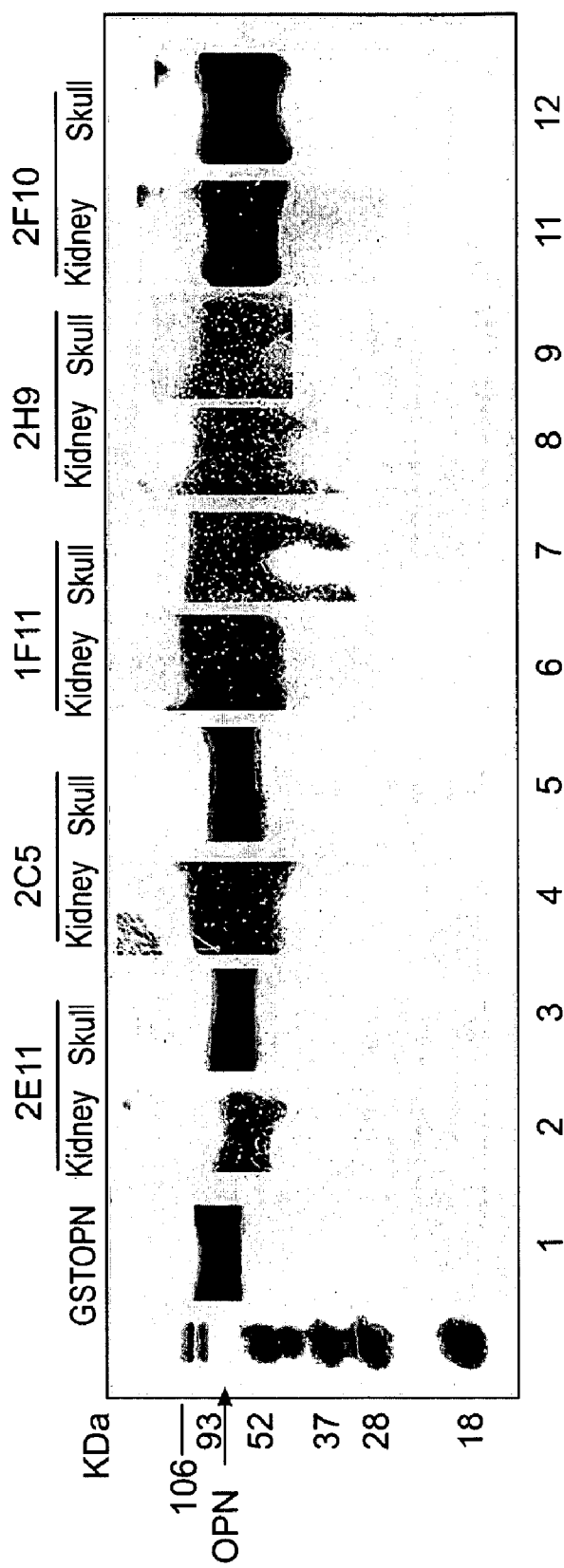
FIG. 8 shows a Western blot analysis of anti-OPN MAbs against native OPN in rat kidney and skull lysate.

Reactivities Against Native OPN. The results above have demonstrated that the five antibodies reacted with recombinant OPN. In order to confirm that they also react with native OPN these five MAbs were used in Western blots to probe proteins from rat skull and kidney tissue lysates (FIG. 8). The analysis was carried out as described in FIG. 5B except the 10-20 µg of lysate proteins samples were loaded in each lane. After electrophoresis and blotting the blot was probed with each MAb and developed with the ECL detection system. The band corresponding to native OPN from those two tissue lysates were identified with the five MAbs, which had similar molecular weights as the positive control (recombinant h-FL OPN of 65 KDa). Similarly, when tissue lysates from wild type, heterozygous and $OPN^{-/-}$ mice were used in the Western blot the OPN bands were present only in the wild type and the heterozygous samples. These results showed that these MAbs interacted with OPN of rat and mouse species.

Figure 9A:
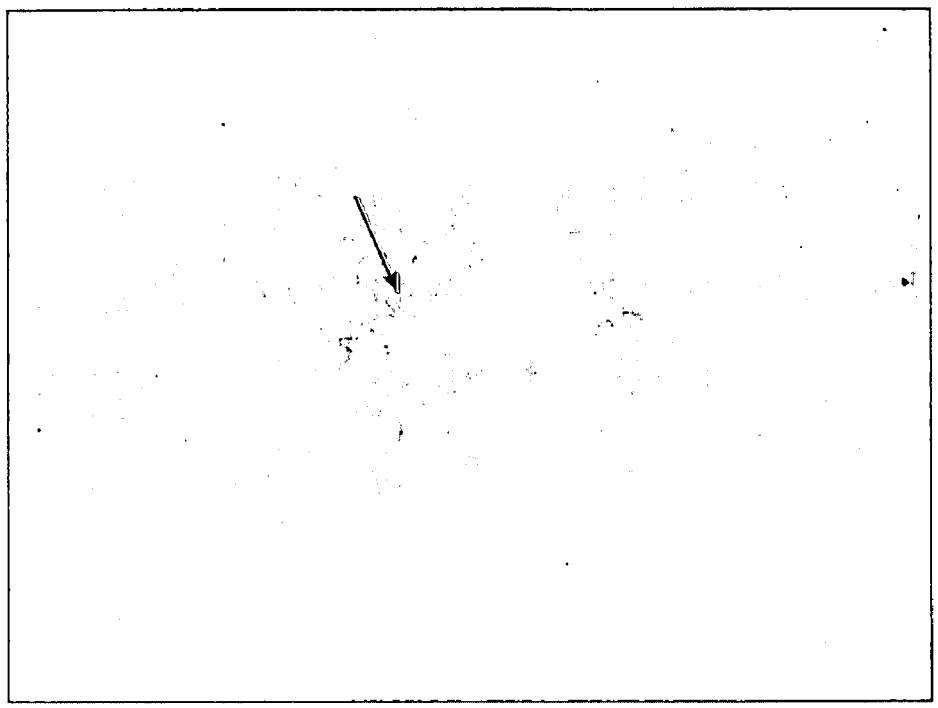
FIG. 9 shows an immunohistochemical analysis of OPN in mouse bone by (9A) a control antibody or (9B & 9C) biotinylated 1F11. (9A) is at 100×, (9B) is at 50× and (9C) is at 200× magnification. (9C) is a high power view of a portion of the field shown in (9B).
Figure 9B:
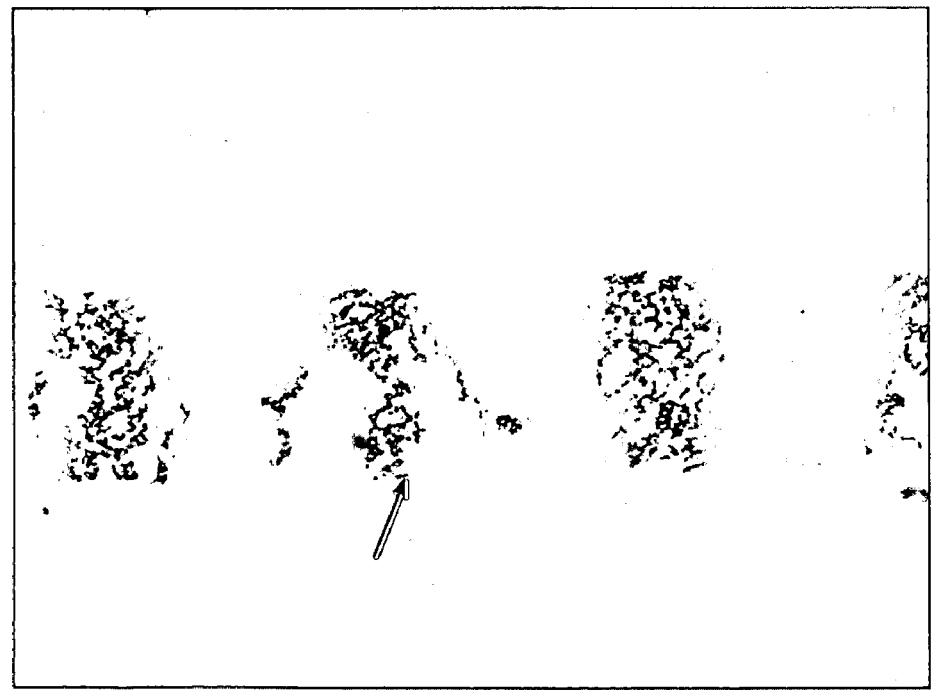
Figure 9C:
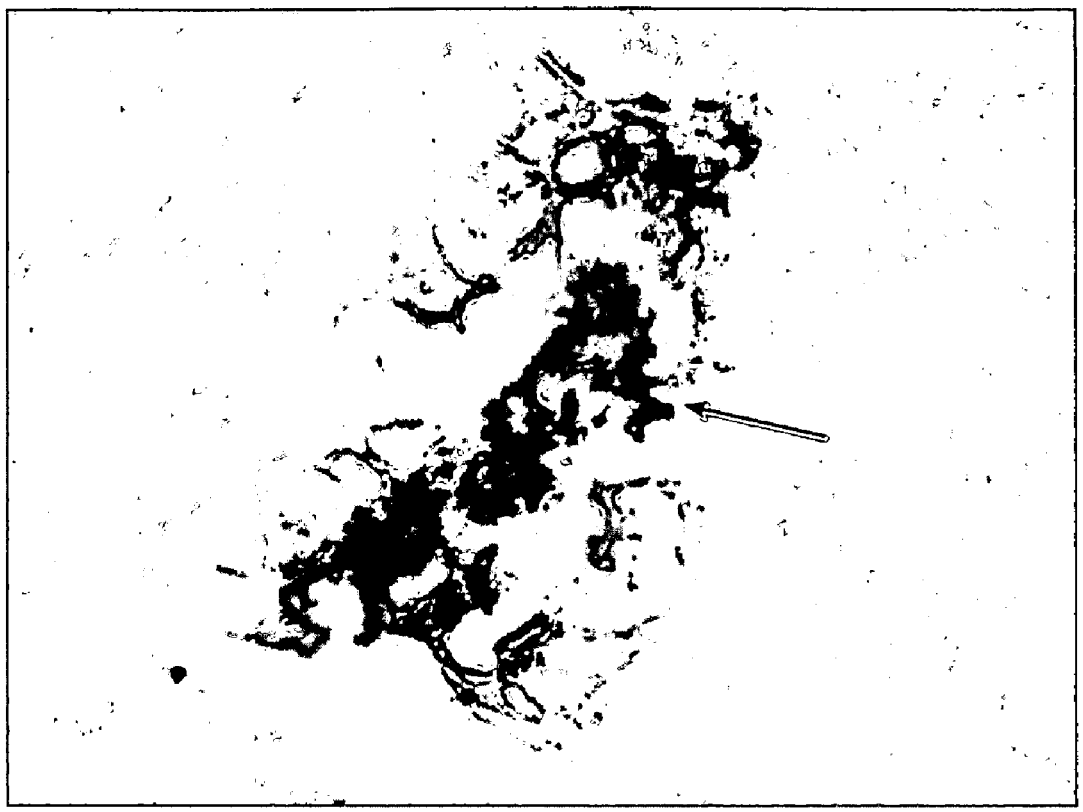

Immunohistochemistry in Mouse Spinal Discs. The ability of the MAbs to bind native OPN in situ was also investigated in animal tissue with immunohistochemistry. Since OPN in mouse embryos indicates that the gene is expressed in early stages of bone formation by some preosteoblasts and osteoblasts and in some cells of the marrow (Mark, et al., J Histochem Cytochem, 35:707-716, 1987; Mark, M. P., et al., Cell Tissue Res, 251:23-30, 1988), biotinylated 1F11 was used to probe OPN in tissue sections of whole embryos from 15-day old wild-type mice. Mouse embryo was fixed in PLP and cryoprotected in 20% sucrose in PBS and then frozen in OCT compound. The thickness of tissue sections was 5 µm. The antigens were retrieve using citrate buffer under high heat. The endogenous peroxidase activity was eliminated by 0.3% hydrogen peroxide and nonspecific binding was blocked by 2% goat serum in 1% PBS-BSA. 3.3 µg/ml of biotinylated 1F11 was used to probe (FIGS. 9B, 9C) and 1.0 µg/ml of purified mouse IgG as a negative control (FIG. 9A). ABC Elit kit and DAB were used as signal detection for test sample slides and 1:100 HRP-goat anti-mouse antibody followed with DAB substrate for negative control. Finally the slides were stained with methylene blue. The low-power view (50×) of embryonic mouse showed strong expression of OPN (dark brown) in mouse spine (FIG. 9B). High-power view (200×) showed the expression of OPN was located the bone sections of the spinal dices (FIG. 9C). The mouse IgG, negative control showed nothing in the spinal bone structure (100×; FIG. 9A). The black arrows were pointed to the bone section on the spinal disc. Intense staining was found in the spinal dices but not in other parts of the bone structure and tissues (FIGS. 9 B, C). In contrast, when a negative control pure mouse IgG irrelevant to OPN was used as the probe, there were no signals in the spinal bone area (FIG. 9A). Therefore, our MAbs were able to specifically detect OPN molecules in situ.

Figure 10A:
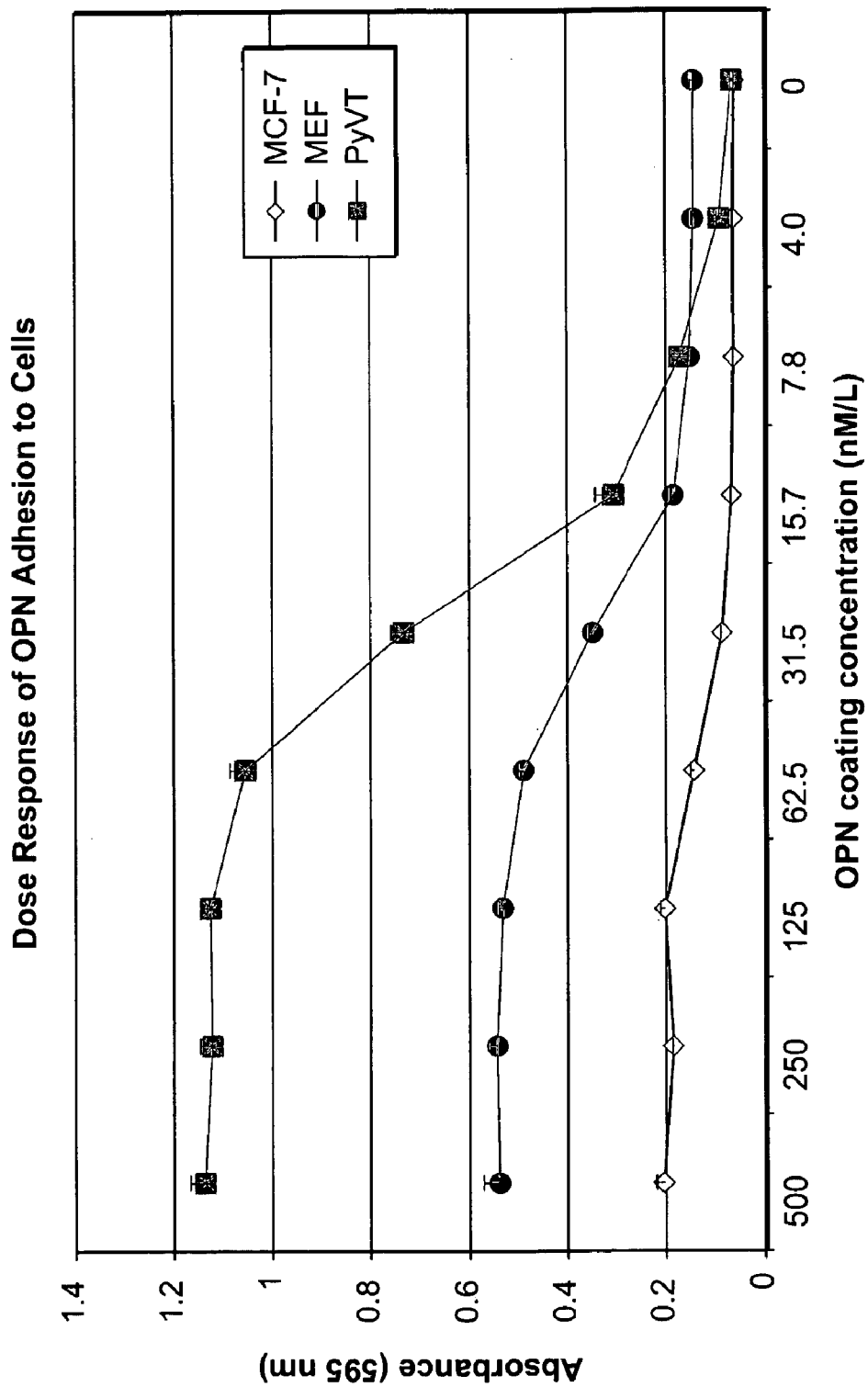
FIG. 10 shows the characterization of the monoclonal antibodies of the present invention for neutralization function against OPN-mediated cell adhesion. (10A) shows a dose response curve of OPN to the non-invasive breast cancer cell line MCF7, mouse embryonic fibroblast cell line (MEF) and mouse mammary tumor cell line (PyVT). (10B) shows MAb inhibition of cell adhesion to OPN.

Cells Adhesion to OPN. Liaw, et al., (1994) showed that OPN promoted cell adhesion in a dose-dependent manner. The MAbs specific for different OPN epitopes present ideal tools to study structure and function relationship of OPN in cell adhesion, using a cell binding inhibition assay. In order to determine the optimal dosage of OPN as a cell adhesion promoting factor, 2-fold serial dilutions of osteopontin from 500 nmol/L to 3.9 nmol/L were used to coat microtiter plate wells. After 30-60 minutes of incubation, the degrees of adhesion to all three-cell lines, MEF, MCF7, and PyVT, reached plateau with OPN at 62.5 nM (as measured by $A_{595nm}$). Further increases in OPN concentration did not improve cell attachment significantly (FIG. 10A). On the other hand, when OPN concentrations were 7.8 nM or less, there was essentially no cell adhesion as shown by insignificant absorbance readings.

Figure 10B:
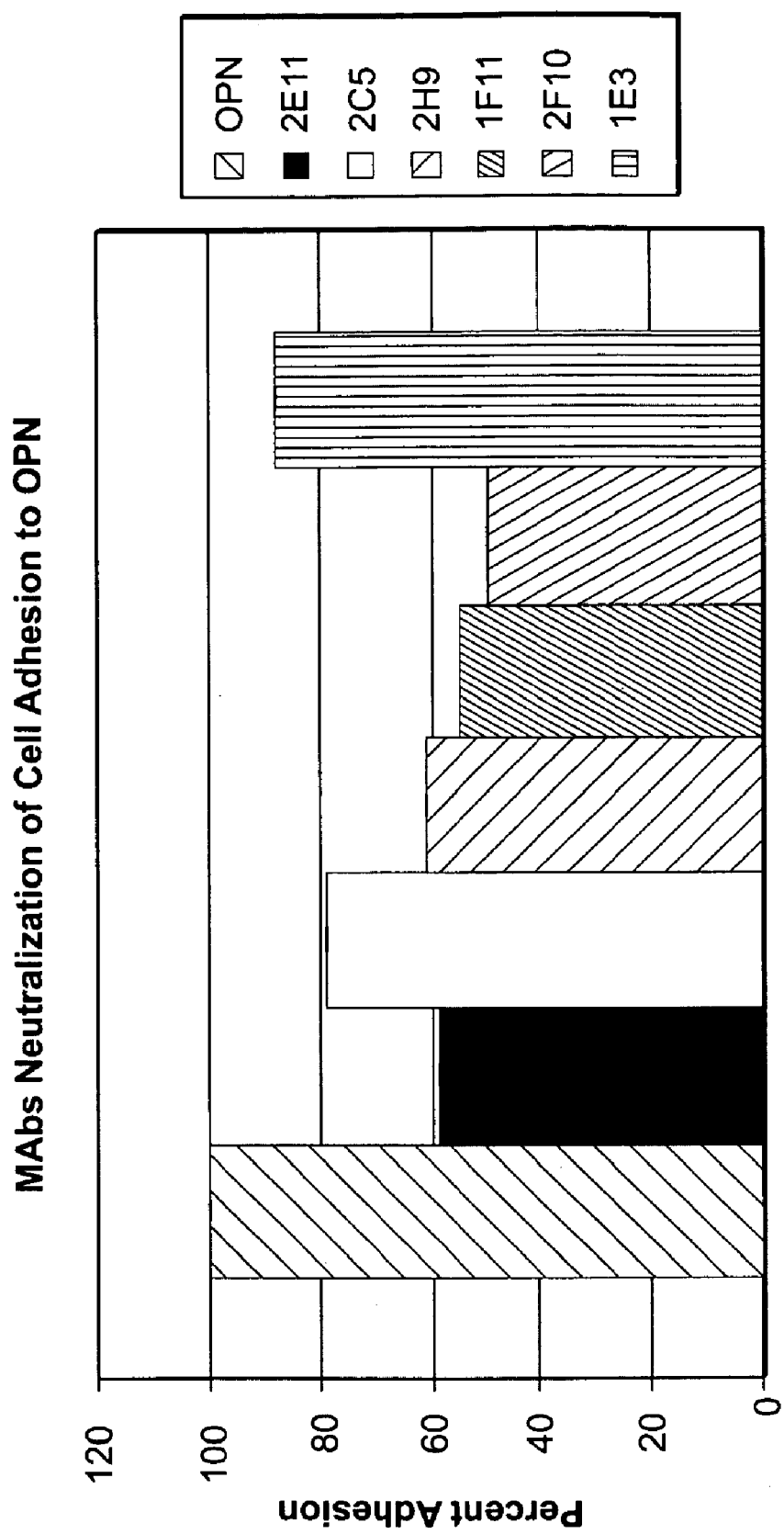

After the optimal OPN concentration was determined, the ability of the MAbs to inhibit cell adhesion was tested. FIG. 10B showed that the five antibodies (tested at saturation concentrations) decreased cell adhesion by ~20-50%, with 2C5 having the least inhibitory effect (21% inhibition) and 2F10 having the most (51% inhibition) (FIG. 10B). This result was consistent with the observation that 2C5 had the lowest activity in ELISA. In contrast, the inhibitory effect was not significant (only 12% inhibition) for 1E3, a control antibody irrelevant to OPN.

Development of Quantitative ELISA for OPN: Optimization of ELISA Conditions. MAb 2F10 specific for the N-terminal of OPN and MAb 1F11 specific for the C terminal were evaluated as a capture-detection antibody pair in a sandwich ELISA for OPN quantification. To aid detection of signals, the detection antibody was biotinylated. In this assay design 2F10 was designated the capture antibody and biotinylated 1F11 was the detection antibody. Hence, this antibody selection ensured that only relatively intact OPN molecules be recognized and quantitatively determined.

The chessboard reagent titration experiments (setting up the assay in a "chessboard" pattern takes into account the variability inherent to the assay plate and the detection system) were carried out to define optimal assay parameters. Representative results from multiple experiments showed that 2F10 at 1.5 µg/ml and 1F11 at 0.6 µg/ml would be the optimal antibody concentrations for the sandwich ELISA.

Figure 11:
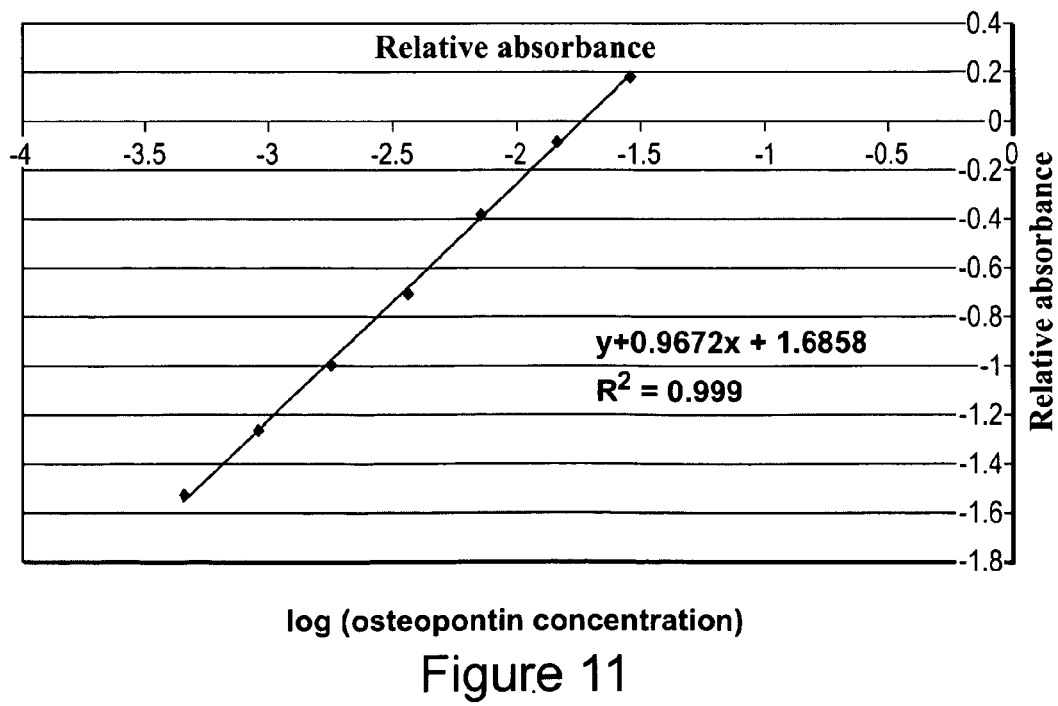
FIG. 11 shows an OPN standard curve generated with a sandwich ELISA. A sandwich ELISA was performed with 2F10 as the capture antibody and biotinylated 1F11 as the detection antibody. A dose curve of human recombinant osteopontin was used. The low range of the samples is depicted here (0.9 ng/ml to 14 pg/ml) to show assay sensitivity. There was a high correlation coefficient with $R^2$=0.99.

Establishment of ELISA for Full-length OPN: Establishment of Standard Curve. There are commercially available kits for the detection of osteopontin. Immunobiological Diagnostics (Minneapolis, Minn.) sells a human osteopontin assay kit that detects full-length osteopontin at a sensitivity of 5 ng/ml, Assay Designs (Ann Arbor, Mich.) offers a human osteopontin enzyme immunometric assay kit with a detection sensitivity of 5 ng/ml, and R&D Systems (Minneapolis, Minn.) has a human osteopontin immunoassay (Quantikine) with undefined sensitivity. All of these assays detect full-length osteopontin protein. As an initial test of our antibodies and to compare our results to the commercially available assays, we developed an ELISA for the detection of full-length osteopontin using two of our antibodies, 2F10 (N-terminal specific) and 1F11 (C-terminal specific). Both antibodies were biotinylated, and used in turn as either the capture or detection antibody in a sandwich ELISA assay. We found that the combination of these antibodies could detect recombinant osteopontin efficiently (FIG. 11), with a conservative sensitivity of approximately 0.45 ng/ml. This result suggests that our assay is more sensitive to low osteopontin levels compared to commercially available assay kits, and that the sandwich ELISA can be developed using our new monoclonal antibodies. Thus, the sandwich ELISA generates a standard curve that can be used to provide accurate determinations of OPN concentrations in test samples.

Levels of Plasma OPN in PTC Patients. In attempt to evaluate OPN as a biomarker for cancer, the sandwich ELISA was applied to measure OPN levels in PTC (papillary thyroid carcinoma) patients. Eighteen healthy controls were analyzed by antigen-capture ELISA to determine the basal plasma OPN levels. Group 1 consists of 4 PTC patient plasma samples and Group 2 consists the other 10 PTC patient plasma samples. OPN levels were higher in both groups of PTC patients (Group 1: mean 16.73 ng/ml, range 0.27-34.59 ng/ml; Group 2: mean 40.56 ng/ml, range 13.06-84.66 ng/ml) (FIGS. 12A, B) than in controls (mean 2.8 ng/ml, range 0-16.76 ng/ml). The percent difference of Group 1 and Group 2 from control population was 78.67 and 213.97%, respectively.

Figures 12A, 12B:
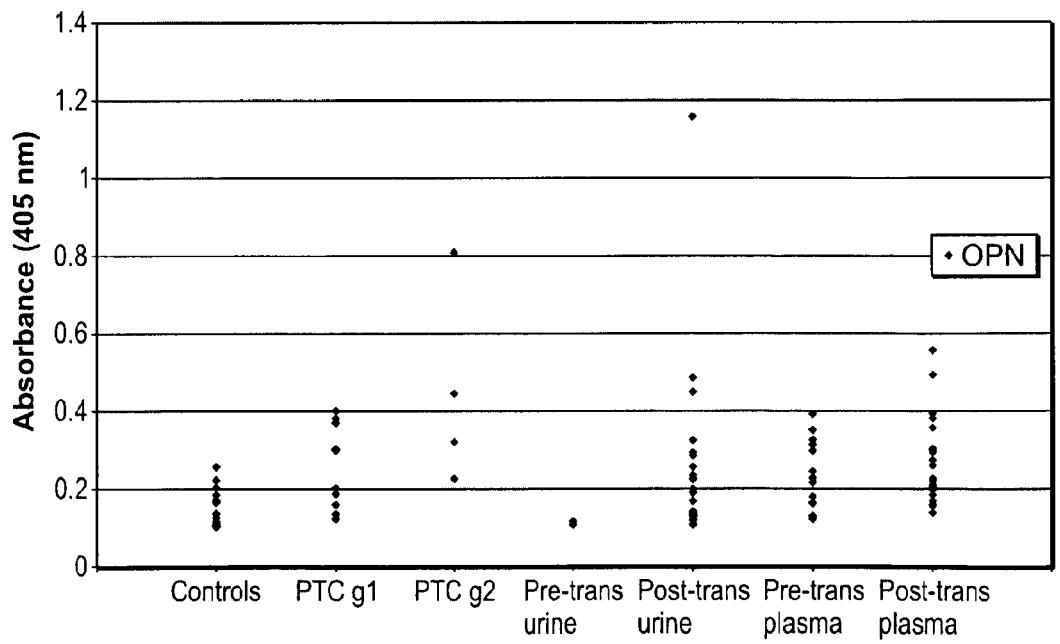
FIG. 12 shows a quantitative analysis of OPN in human papillary carcinoma (PTC) and kidney transplant patients using a sandwich ELISA. (12A) shows the mean concentration for each group. (12B) shows the distribution of individual absorbency values for each group.

OPN Levels in of Plasma OPN in Bodily Fluids of Kidney Transplant Patients. The OPN level from pre- and post-kidney transplant patients' urine and plasma samples were measured in the sandwich ELISA for OPN quantification. Neat samples (plasma or urine) at 50 µl/well were loaded on top of precoated capture antibody 2F10 followed by addition of biotinylated monoclonal antibody 1F11 (detecting antibody). HRP-conjugated streptavidin and TMB substrate were added to develop color. FIG. 12A shows the mean concentration for each group was derived using the mean $A_{405nm}$ value read against the standard curve in FIG. 11. Percent difference= (Sample Mean Concentration−Normal Mean concentration)/ Normal Mean Concentration×100. FIG. 12B shows the distribution of individual $A_{405nm}$ values for each group. Three data point from the control group ($A_{405nm}$=0.631, 0.608 and 0.506) were considered outliers and removed from the data analysis. All patient samples were represented here and included in the calculations. The post-urine, pre-and post-plasma samples showed higher OPN level than controls (mean of post-urine 16.38, range 0-127.84, mean of pre-plasma 13.79, range 0.15-33.49, mean of post-plasma 18.16, range 2.24-53.78). The percent differences of kidney transplant patient's samples from control were 76.72, 62, and 86.79% respectively (FIGS. 12A, B). Urine OPN level from pre-transplant patients samples did not show significant differences from the control group. Additionally, post-transplant samples (plasma and urine) had higher OPN levels than their pre-transplant counterparts, probably because of the wound resulted from transplantation surgery (Liaw, et al., 1998).

We claim:

1. A method of determining the presence of C-terminal fragments of osteopontin in a sample suspected of comprising C-terminal fragments of osteopontin, the method comprising:
   a) providing i) a sample suspected of containing C terminal osteopontin fragments from which full length osteopontin and fragments of osteopontin comprising N-terminal amino acid residues of osteopontin have been removed or separated from any C-terminal fragments present and ii) one or more antibodies specific for epitopes located on the C-terminal of osteopontin selected from the group consisting of 2E11 produced by a hybridoma deposited as ATCC Accession No. PTA-11449 and 1F11 produced by a hybridoma deposited as ATCC Accession No. PTA-11448;
   b) determining the presence of C-terminal fragments of osteopontin by determining specific binding of fragments in the sample with the one or more antibodies of step a).

2. The method of claim 1, wherein said antibodies specific for epitopes located on the C-terminal of osteopontin are specific for epitopes located at amino acids 167-314 or amino acids 169-314 of the C-terminus of the osteopontin peptide.

3. The method of claim 1, wherein said method is automated.

4. A method of determining the presence of N-terminal fragments of osteopontin in a sample suspected of comprising N-terminal fragments of osteopontin, the method comprising:

a) providing i) a sample suspected of containing N-terminal osteopontin fragments from which full length osteopontin and fragments of osteopontin comprising C-terminal amino acid residues of osteopontin have been removed or separated from any N-terminal amino acid residues present and ii) one or more antibodies specific for epitopes located on the N-terminal of osteopontin selected from the group consisting of 2C5 produced by a hybridoma deposited as ATCC Accession No. PTA-11447, 2H9 produced by a hybridoma deposited as ATCC Accession No. PTA-11446 and 2F10 produced by a hybridoma deposited as ATCC Accession No. PTA-11450;

b) determining the presence of N-terminal fragments of osteopontin by determining specific binding of fragments in the sample with the one or more antibodies of step a).

5. The method of claim 4, wherein said antibodies specific for epitopes located on the N-terminal of osteopontin are specific for epitopes located at amino acids 1-166 or amino acids 1-168 of the N-terminus of the osteopontin peptide.

6. The method of claim 4, wherein said method is automated.

* * * * *